(12) United States Patent
Funke et al.

(10) Patent No.: US 7,556,723 B2
(45) Date of Patent: Jul. 7, 2009

(54) ELECTRODE DESIGN FOR BIOSENSOR

(75) Inventors: Tom Funke, Carmel, IN (US); Abner D. Joseph, Carmel, IN (US); Randall K. Riggles, Indianapolis, IN (US)

(73) Assignees: Roche Diagnostics Operations, Inc., Indianapolis, IN (US); Roche Operations Ltd., Hamilton (BM)

( * ) Notice: Subject to any disclaimer, the term of this patent is extended or adjusted under 35 U.S.C. 154(b) by 733 days.

(21) Appl. No.: 11/033,704

(22) Filed: Jan. 12, 2005

(65) Prior Publication Data

US 2005/0284758 A1    Dec. 29, 2005

Related U.S. Application Data

(63) Continuation-in-part of application No. 10/961,352, filed on Oct. 8, 2004, now abandoned.

(60) Provisional application No. 60/581,002, filed on Jun. 18, 2004.

(51) Int. Cl.
    *G01N 27/327* (2006.01)
(52) U.S. Cl. .................. 204/403.02; 204/416
(58) Field of Classification Search ..................
    204/403.01–403.15, 416–418
    See application file for complete search history.

(56) References Cited

U.S. PATENT DOCUMENTS

| 3,526,480 A | 9/1970 | Findl et al. |
| 3,551,295 A | 12/1970 | Dyer |
| 3,621,381 A | 11/1971 | Eckfeldt |
| 3,715,192 A | 2/1973 | Wenz et al. |
| 3,720,093 A | 3/1973 | Gill |
| 3,763,422 A | 10/1973 | MacPhee et al. |
| 3,770,607 A | 11/1973 | Williams |
| 3,776,832 A | 12/1973 | Oswin et al. |
| 3,838,033 A | 9/1974 | Mindt et al. |
| 3,902,970 A | 9/1975 | Levin |

(Continued)

FOREIGN PATENT DOCUMENTS

AU        737 787        8/2001

(Continued)

OTHER PUBLICATIONS

Aoki et al., "Quantitative Analysis Of Reversible Diffusion Controlled Currents of Redox Soluble Species At Interdigitated Array Electrodes Under Steady-State Conditions", J. Electroanal. Chem. 256 (1988) 269-282.

(Continued)

*Primary Examiner*—Alex Noguerola
(74) *Attorney, Agent, or Firm*—Woodard, Emhardt, Moriarty, McNett & Henry LLP

(57) ABSTRACT

A test strip for measuring a signal of interest in a biological fluid when the test strip is mated to an appropriate test meter, wherein the test strip and the test meter include structures to verify the integrity of the test strip traces, to measure the parasitic resistance of the test strip traces, and to provide compensation in the voltage applied to the test strip to account for parasitic resistive losses in the test strip traces. In addition, conductive traces are positioned to ensure structural interrogation of all electrodes and traces present upon the test strip.

19 Claims, 10 Drawing Sheets

U.S. PATENT DOCUMENTS

| | | |
|---|---|---|
| 3,919,627 A | 11/1975 | Allen |
| 3,925,183 A | 12/1975 | Oswin et al. |
| 3,937,615 A | 2/1976 | Clack et al. |
| 3,980,437 A | 9/1976 | Kishimoto et al. |
| 4,005,002 A | 1/1977 | Racine et al. |
| 4,008,448 A | 2/1977 | Muggli |
| 4,040,908 A | 8/1977 | Clark, Jr. |
| 4,053,381 A | 10/1977 | Hamblen et al. |
| 4,065,263 A | 12/1977 | Woodbridge, III |
| 4,086,631 A | 4/1978 | Vick |
| 4,123,701 A | 10/1978 | Josefsen et al. |
| 4,127,448 A | 11/1978 | Schick et al. |
| 4,184,936 A | 1/1980 | Paul et al. |
| 4,214,968 A | 7/1980 | Battaglia et al. |
| 4,217,196 A | 8/1980 | Huch |
| 4,224,125 A | 9/1980 | Nakamura et al. |
| 4,225,410 A | 9/1980 | Pace |
| 4,230,537 A | 10/1980 | Delente et al. |
| 4,233,029 A | 11/1980 | Columbus |
| 4,260,680 A | 4/1981 | Muramatsu et al. |
| 4,263,343 A | 4/1981 | Kim |
| 4,265,250 A | 5/1981 | Parker |
| 4,273,134 A | 6/1981 | Ricciardelli |
| 4,273,639 A | 6/1981 | Gottermeier |
| 4,297,569 A | 10/1981 | Flies |
| 4,301,412 A | 11/1981 | Hill et al. |
| 4,303,887 A | 12/1981 | Hill et al. |
| 4,323,536 A | 4/1982 | Columbus |
| 4,329,642 A | 5/1982 | Luthi et al. |
| 4,366,033 A | 12/1982 | Richter et al. |
| 4,407,290 A | 10/1983 | Wilber |
| 4,407,959 A | 10/1983 | Tsuji et al. |
| 4,413,407 A | 11/1983 | Columbus |
| 4,413,628 A | 11/1983 | Tamulis |
| 4,420,564 A | 12/1983 | Tsuji et al. |
| 4,431,004 A | 2/1984 | Bessman et al. |
| 4,436,094 A | 3/1984 | Cerami |
| 4,440,175 A | 4/1984 | Wilkins |
| 4,476,149 A | 10/1984 | Poppe et al. |
| 4,477,314 A | 10/1984 | Richter et al. |
| 4,477,575 A | 10/1984 | Vogel et al. |
| 4,499,423 A | 2/1985 | Matthiessen |
| 4,510,383 A | 4/1985 | Ruppender |
| 4,517,291 A | 5/1985 | Seago |
| 4,545,382 A | 10/1985 | Higgins et al. |
| 4,547,735 A | 10/1985 | Kiesewetter et al. |
| 4,552,458 A | 11/1985 | Lowne |
| 4,571,292 A | 2/1986 | Liu et al. |
| 4,578,716 A | 3/1986 | van Rijckevorsel et al. |
| 4,592,893 A | 6/1986 | Poppe et al. |
| 4,628,193 A | 12/1986 | Blum |
| 4,642,295 A | 2/1987 | Baker |
| 4,648,665 A | 3/1987 | Davis et al. |
| 4,652,830 A | 3/1987 | Brown |
| 4,654,197 A | 3/1987 | Lilja et al. |
| 4,671,288 A | 6/1987 | Gough |
| 4,676,653 A | 6/1987 | Strohmeier et al. |
| 4,679,562 A | 7/1987 | Luksha |
| 4,682,602 A | 7/1987 | Prohaska |
| 4,686,479 A | 8/1987 | Young et al. |
| 4,703,017 A | 10/1987 | Campbell et al. |
| 4,703,756 A | 11/1987 | Gough et al. |
| 4,711,245 A | 12/1987 | Higgins et al. |
| 4,713,347 A | 12/1987 | Mitchell et al. |
| 4,714,874 A | 12/1987 | Morris et al. |
| 4,731,726 A | 3/1988 | Allen, III |
| 4,734,184 A | 3/1988 | Burleigh et al. |
| 4,750,496 A | 6/1988 | Reinhart et al. |
| 4,759,828 A | 7/1988 | Young et al. |
| 4,789,804 A | 12/1988 | Karube et al. |
| 4,795,542 A | 1/1989 | Ross et al. |
| 4,797,256 A | 1/1989 | Watlington, IV |
| 4,805,624 A | 2/1989 | Yao et al. |
| 4,806,311 A | 2/1989 | Greenquist |
| 4,806,312 A | 2/1989 | Greenquist |
| 4,810,203 A | 3/1989 | Komatsu |
| 4,816,224 A | 3/1989 | Vogel et al. |
| 4,820,399 A | 4/1989 | Senda et al. |
| 4,820,636 A | 4/1989 | Hill et al. |
| 4,832,814 A | 5/1989 | Root |
| 4,834,234 A | 5/1989 | Sacherer et al. |
| 4,849,330 A | 7/1989 | Humphries et al. |
| 4,865,873 A | 9/1989 | Cole, Jr. et al. |
| 4,877,580 A | 10/1989 | Aronowitz et al. |
| 4,897,162 A | 1/1990 | Lewandowski et al. |
| 4,897,173 A | 1/1990 | Nankai et al. |
| 4,919,770 A | 4/1990 | Preidel et al. |
| 4,927,516 A | 5/1990 | Yamaguchi et al. |
| 4,935,105 A | 6/1990 | Churchouse |
| 4,935,106 A | 6/1990 | Liston et al. |
| 4,935,346 A | 6/1990 | Phillips et al. |
| 4,938,860 A | 7/1990 | Wogoman |
| 4,940,945 A | 7/1990 | Littlejohn et al. |
| 4,954,087 A | 9/1990 | Lauks et al. |
| 4,956,275 A | 9/1990 | Zuk et al. |
| 4,963,814 A | 10/1990 | Parks et al. |
| 4,970,145 A | 11/1990 | Bennetto et al. |
| 4,975,647 A | 12/1990 | Downer et al. |
| 4,976,724 A | 12/1990 | Nieto et al. |
| 4,999,582 A | 3/1991 | Parks et al. |
| 4,999,632 A | 3/1991 | Parks |
| 5,018,164 A | 5/1991 | Brewer et al. |
| 5,019,974 A | 5/1991 | Beckers |
| 5,035,862 A | 7/1991 | Dietze et al. |
| 5,039,618 A | 8/1991 | Stone |
| 5,049,487 A | 9/1991 | Phillips et al. |
| 5,053,199 A | 10/1991 | Keiser et al. |
| 5,059,394 A | 10/1991 | Phillips et al. |
| 5,066,372 A | 11/1991 | Weetall |
| 5,075,077 A | 12/1991 | Durley, III et al. |
| 5,096,669 A | 3/1992 | Lauks et al. |
| 5,108,564 A | 4/1992 | Szuminsky et al. |
| 5,112,455 A | 5/1992 | Cozzette et al. |
| 5,112,758 A | 5/1992 | Fellman et al. |
| 5,118,183 A | 6/1992 | Cargill et al. |
| 5,120,420 A | 6/1992 | Nankai et al. |
| 5,122,244 A | 6/1992 | Hoenes et al. |
| 5,126,952 A | 6/1992 | Kildal-Brandt et al. |
| 5,128,015 A | 7/1992 | Szuminsky et al. |
| 5,141,850 A | 8/1992 | Cole et al. |
| 5,141,868 A | 8/1992 | Shanks et al. |
| 5,143,694 A | 9/1992 | Schafer et al. |
| 5,179,005 A | 1/1993 | Phillips et al. |
| 5,179,288 A | 1/1993 | Miffitt et al. |
| 5,182,707 A | 1/1993 | Cooper et al. |
| 5,187,100 A | 2/1993 | Matzinger et al. |
| 5,192,415 A | 3/1993 | Yoshioka et al. |
| 5,220,920 A | 6/1993 | Gharib |
| 5,232,516 A | 8/1993 | Hed |
| 5,232,668 A | 8/1993 | Grant et al. |
| 5,234,813 A | 8/1993 | McGeehan et al. |
| 5,243,516 A | 9/1993 | White |
| 5,246,858 A | 9/1993 | Arbuckle et al. |
| 5,250,439 A | 10/1993 | Musho et al. |
| 5,264,103 A | 11/1993 | Yoshioka et al. |
| 5,266,179 A | 11/1993 | Nankai et al. |
| 5,269,891 A | 12/1993 | Colin |
| 5,279,294 A | 1/1994 | Anderson et al. |
| 5,281,395 A | 1/1994 | Markart et al. |
| 5,284,770 A | 2/1994 | Adrian et al. |
| 5,286,362 A | 2/1994 | Hoenes et al. |
| 5,288,636 A | 2/1994 | Pollmann et al. |
| 5,296,192 A | 3/1994 | Carroll et al. |
| 5,304,468 A | 4/1994 | Phillips et al. |

| | | | | | |
|---|---|---|---|---|---|
| 5,306,623 A | 4/1994 | Kiser | 5,645,798 A | 7/1997 | Schreiber et al. |
| 5,311,426 A | 5/1994 | Donohue et al. | 5,650,061 A | 7/1997 | Kuhr et al. |
| 5,312,762 A | 5/1994 | Guiseppi-Elie | 5,650,062 A | 7/1997 | Ikeda et al. |
| 5,344,754 A | 9/1994 | Zweig | 5,653,863 A | 8/1997 | Genshaw et al. |
| 5,352,351 A | 10/1994 | White et al. | 5,654,178 A | 8/1997 | Fitzpatrick et al. |
| 5,353,351 A | 10/1994 | Bartoli et al. | 5,656,502 A | 8/1997 | MacKay et al. |
| 5,366,609 A | 11/1994 | White et al. | 5,658,443 A | 8/1997 | Yamamoto et al. |
| 5,371,687 A | 12/1994 | Holmes, II et al. | 5,658,802 A | 8/1997 | Hayes et al. |
| 5,376,254 A | 12/1994 | Fisher | 5,665,215 A | 9/1997 | Bussmann et al. |
| 5,379,214 A | 1/1995 | Arbuckle et al. | 5,670,031 A | 9/1997 | Hintsche et al. |
| 5,385,846 A | 1/1995 | Kuhn et al. | 5,682,884 A | 11/1997 | Hill et al. |
| 5,389,215 A | 2/1995 | Horiuchi et al. | 5,686,659 A | 11/1997 | Neel et al. |
| 5,395,504 A | 3/1995 | Saurer et al. | 5,691,486 A | 11/1997 | Behringer et al. |
| 5,405,511 A | 4/1995 | Brown et al. | 5,691,633 A | 11/1997 | Liu et al. |
| 5,411,647 A | 5/1995 | Johnson et al. | 5,695,623 A | 12/1997 | Michel et al. |
| 5,413,690 A | 5/1995 | Kost et al. | 5,698,083 A | 12/1997 | Glass |
| 5,413,764 A | 5/1995 | Haar | 5,700,695 A | 12/1997 | Yassinzadeh et al. |
| 5,418,142 A | 5/1995 | Kiser et al. | 5,708,247 A | 1/1998 | McAleer et al. |
| 5,421,189 A | 6/1995 | Dussault | 5,710,622 A | 1/1998 | Neel et al. |
| 5,424,035 A | 6/1995 | Hones et al. | 5,719,667 A | 2/1998 | Miers |
| 5,426,032 A | 6/1995 | Phillips et al. | 5,720,862 A | 2/1998 | Hamamoto et al. |
| 5,437,772 A | 8/1995 | De Castro et al. | 5,723,284 A | 3/1998 | Ye |
| 5,437,999 A | 8/1995 | Diebold et al. | 5,727,548 A | 3/1998 | Hill et al. |
| 5,438,271 A | 8/1995 | White et al. | 5,728,074 A | 3/1998 | Castellano et al. |
| 5,439,826 A | 8/1995 | Kontorovich | 5,745,308 A | 4/1998 | Spangenberg |
| 5,445,967 A | 8/1995 | Deuter | 5,757,666 A | 5/1998 | Schreiber et al. |
| 5,447,837 A | 9/1995 | Urnovitz | 5,759,794 A | 6/1998 | Levine et al. |
| 5,453,360 A | 9/1995 | Yu | 5,762,770 A | 6/1998 | Pritchard et al. |
| 5,469,846 A | 11/1995 | Khan | 5,776,710 A | 7/1998 | Levine et al. |
| 5,470,533 A | 11/1995 | Shindo et al. | 5,780,304 A | 7/1998 | Matzinger et al. |
| 5,477,326 A | 12/1995 | Dosmann | 5,786,584 A | 7/1998 | Button et al. |
| 5,489,414 A | 2/1996 | Schreiber et al. | 5,788,833 A | 8/1998 | Lewis et al. |
| 5,494,638 A | 2/1996 | Gullick | 5,789,255 A | 8/1998 | Yu |
| 5,500,350 A | 3/1996 | Baker et al. | 5,792,668 A | 8/1998 | Deamer et al. |
| 5,504,011 A | 4/1996 | Gavin et al. | 5,798,031 A | 8/1998 | Charlton et al. |
| 5,508,171 A | 4/1996 | Walling et al. | 5,801,057 A | 9/1998 | Smart et al. |
| 5,508,200 A | 4/1996 | Tiffany et al. | 5,820,551 A | 10/1998 | Hill et al. |
| 5,508,203 A | 4/1996 | Fuller et al. | 5,820,622 A | 10/1998 | Gross et al. |
| 5,509,410 A | 4/1996 | Hill et al. | 5,832,921 A | 11/1998 | Lennert et al. |
| 5,515,170 A | 5/1996 | Matzinger | 5,834,217 A | 11/1998 | Levine et al. |
| 5,515,847 A | 5/1996 | Braig et al. | 5,837,546 A | 11/1998 | Allen et al. |
| 5,526,111 A | 6/1996 | Collins et al. | 5,843,691 A | 12/1998 | Douglas et al. |
| 5,526,120 A | 6/1996 | Jina et al. | 5,843,692 A | 12/1998 | Phillips et al. |
| 5,526,808 A | 6/1996 | Kaminsky | 5,846,744 A | 12/1998 | Athey et al. |
| 5,532,128 A | 7/1996 | Eggers et al. | 5,849,174 A | 12/1998 | Sanghera et al. |
| 5,552,116 A | 9/1996 | Yokota et al. | 5,856,195 A | 1/1999 | Charlton et al. |
| 5,554,531 A | 9/1996 | Zweig | 5,873,990 A | 2/1999 | Wojciechowski et al. |
| 5,556,789 A | 9/1996 | Goerlach-Graw et al. | 5,883,378 A | 3/1999 | Irish et al. |
| 5,563,031 A | 10/1996 | Yu | 5,885,839 A | 3/1999 | Lingane et al. |
| 5,563,042 A | 10/1996 | Phillips et al. | 5,890,489 A | 4/1999 | Elden |
| 5,569,591 A | 10/1996 | Kell et al. | 5,904,898 A | 5/1999 | Markart |
| 5,569,608 A | 10/1996 | Sommer | 5,911,872 A | 6/1999 | Lewis et al. |
| 5,572,159 A | 11/1996 | McFarland | 5,916,156 A | 6/1999 | Hildenbrand et al. |
| 5,575,895 A | 11/1996 | Ikeda et al. | 5,921,925 A | 7/1999 | Cartmell et al. |
| 5,576,073 A | 11/1996 | Kickelhain | 5,922,530 A | 7/1999 | Yu |
| 5,580,794 A | 12/1996 | Allen | 5,922,591 A | 7/1999 | Anderson et al. |
| 5,582,697 A | 12/1996 | Ikeda et al. | 5,925,021 A | 7/1999 | Castellano et al. |
| 5,593,390 A | 1/1997 | Castellano et al. | 5,945,341 A | 8/1999 | Howard, III |
| 5,593,739 A | 1/1997 | Kickelhain | 5,948,289 A | 9/1999 | Noda et al. |
| 5,594,906 A | 1/1997 | Holmes, II et al. | 5,951,836 A | 9/1999 | McAleer et al. |
| 5,597,532 A | 1/1997 | Connolly | 5,965,380 A | 10/1999 | Heller |
| 5,604,110 A | 2/1997 | Baker et al. | 5,968,760 A | 10/1999 | Phillips et al. |
| 5,605,662 A | 2/1997 | Heller et al. | 5,971,923 A | 10/1999 | Finger |
| 5,605,837 A | 2/1997 | Karimi et al. | 5,989,917 A | 11/1999 | McAleer et al. |
| 5,611,900 A | 3/1997 | Worden et al. | 5,997,817 A | 12/1999 | Crismore et al. |
| 5,620,579 A | 4/1997 | Genshaw et al. | 6,004,441 A | 12/1999 | Fujiwara et al. |
| 5,620,863 A | 4/1997 | Tomasco et al. | 6,013,170 A | 1/2000 | Meade |
| 5,628,890 A | 5/1997 | Carter et al. | 6,042,714 A | 3/2000 | Lin et al. |
| 5,630,986 A | 5/1997 | Charlton et al. | 6,044,285 A | 3/2000 | Chaiken et al. |
| 5,635,362 A | 6/1997 | Levine et al. | 6,045,567 A | 4/2000 | Taylor et al. |
| 5,635,364 A | 6/1997 | Clark et al. | 6,061,128 A | 5/2000 | Zweig et al. |
| 5,639,671 A | 6/1997 | Bogart et al. | 6,071,391 A | 6/2000 | Gotoh et al. |
| 5,642,734 A | 7/1997 | Ruben et al. | 6,087,182 A | 7/2000 | Jeng et al. |

| | | |
|---|---|---|
| 6,091,975 A | 7/2000 | Daddona et al. |
| 6,102,872 A | 8/2000 | Doneen et al. |
| 6,103,033 A | 8/2000 | Say et al. |
| 6,120,676 A | 9/2000 | Heller et al. |
| 6,121,009 A | 9/2000 | Heller et al. |
| 6,121,050 A | 9/2000 | Han |
| 6,126,609 A | 10/2000 | Keith et al. |
| 6,128,519 A | 10/2000 | Say |
| 6,129,823 A | 10/2000 | Hughes et al. |
| 6,134,461 A | 10/2000 | Say et al. |
| 6,136,549 A | 10/2000 | Feistel |
| 6,136,610 A | 10/2000 | Polito et al. |
| 6,143,164 A | 11/2000 | Heller et al. |
| 6,143,247 A | 11/2000 | Sheppard, Jr. et al. |
| 6,144,869 A | 11/2000 | Berner et al. |
| 6,150,124 A | 11/2000 | Riedel |
| 6,153,069 A | 11/2000 | Pottgen et al. |
| RE36,991 E | 12/2000 | Yamamoto et al. |
| 6,156,051 A | 12/2000 | Schraga |
| 6,156,173 A | 12/2000 | Gotoh et al. |
| 6,159,745 A | 12/2000 | Roberts et al. |
| 6,162,611 A | 12/2000 | Heller et al. |
| 6,162,639 A | 12/2000 | Douglas |
| 6,168,563 B1 | 1/2001 | Brown |
| 6,168,957 B1 | 1/2001 | Matzinger et al. |
| 6,170,318 B1 | 1/2001 | Lewis |
| 6,174,420 B1 | 1/2001 | Hodges et al. |
| 6,175,752 B1 | 1/2001 | Say et al. |
| 6,176,988 B1 | 1/2001 | Kessler |
| 6,179,979 B1 | 1/2001 | Hodges et al. |
| 6,180,062 B1 | 1/2001 | Naka et al. |
| 6,180,416 B1 | 1/2001 | Kurnik et al. |
| 6,193,873 B1 | 2/2001 | Ohara et al. |
| 6,197,040 B1 | 3/2001 | LeVaughn et al. |
| 6,200,773 B1 | 3/2001 | Ouyang et al. |
| 6,201,607 B1 | 3/2001 | Roth et al. |
| 6,203,952 B1 | 3/2001 | O'Brien et al. |
| 6,206,282 B1 | 3/2001 | Hayes, Sr. et al. |
| 6,206,292 B1 | 3/2001 | Robertz et al. |
| 6,218,571 B1 | 4/2001 | Zheng et al. |
| 6,225,078 B1 | 5/2001 | Ikeda et al. |
| 6,226,081 B1 | 5/2001 | Fantone et al. |
| 6,241,862 B1 | 6/2001 | McAleer et al. |
| 6,246,330 B1 | 6/2001 | Nielsen |
| 6,246,966 B1 | 6/2001 | Perry |
| 6,251,260 B1 | 6/2001 | Heller et al. |
| 6,258,229 B1 | 7/2001 | Winarta et al. |
| 6,258,254 B1 | 7/2001 | Miyamoto et al. |
| 6,259,937 B1 | 7/2001 | Schulman et al. |
| 6,261,519 B1 | 7/2001 | Harding et al. |
| 6,262,749 B1 | 7/2001 | Finger et al. |
| 6,268,162 B1 | 7/2001 | Phillips et al. |
| 6,270,637 B1 | 8/2001 | Crismore et al. |
| 6,271,044 B1 | 8/2001 | Ballerstadt et al. |
| 6,272,364 B1 | 8/2001 | Kurnik |
| 6,277,641 B1 | 8/2001 | Yager |
| 6,281,006 B1 | 8/2001 | Heller et al. |
| 6,284,125 B1 | 9/2001 | Hodges et al. |
| 6,284,550 B1 | 9/2001 | Carroll et al. |
| 6,287,451 B1 | 9/2001 | Winarta et al. |
| 6,287,595 B1 | 9/2001 | Loewy et al. |
| 6,287,875 B1 | 9/2001 | Geisberg |
| 6,294,281 B1 | 9/2001 | Heller |
| 6,295,506 B1 | 9/2001 | Heinonen et al. |
| 6,299,757 B1 | 10/2001 | Feldman et al. |
| 6,300,123 B1 | 10/2001 | Vadgama et al. |
| 6,300,142 B1 | 10/2001 | Andrews et al. |
| 6,300,961 B1 | 10/2001 | Finger et al. |
| 6,309,526 B1 | 10/2001 | Fujiwara et al. |
| 6,315,951 B1 | 11/2001 | Markart |
| 6,316,264 B1 | 11/2001 | Corey et al. |
| 6,325,917 B1 | 12/2001 | Maxwell et al. |
| 6,326,160 B1 | 12/2001 | Dunn et al. |
| 6,329,161 B1 | 12/2001 | Heller et al. |
| 6,330,464 B1 | 12/2001 | Colvin, Jr. et al. |
| 6,335,203 B1 | 1/2002 | Patel et al. |
| 6,338,790 B1 | 1/2002 | Feldman et al. |
| 6,340,428 B1 | 1/2002 | Ikeda et al. |
| 6,342,364 B1 | 1/2002 | Watanabe et al. |
| 6,349,230 B1 | 2/2002 | Kawanaka |
| 6,358,752 B1 | 3/2002 | Durst et al. |
| 6,377,894 B1 | 4/2002 | Deweese et al. |
| 6,377,896 B1 | 4/2002 | Sato et al. |
| 6,379,513 B1 | 4/2002 | Chambers et al. |
| 6,389,891 B1 | 5/2002 | D'Angelico et al. |
| 6,391,558 B1 | 5/2002 | Henkens et al. |
| 6,391,645 B1 | 5/2002 | Huang et al. |
| 6,394,952 B1 | 5/2002 | Anderson et al. |
| 6,395,227 B1 | 5/2002 | Kiser et al. |
| 6,399,258 B2 | 6/2002 | O'Brien et al. |
| 6,401,532 B2 | 6/2002 | Lubbers |
| 6,413,213 B1 | 7/2002 | Essenpreis et al. |
| 6,413,395 B1 | 7/2002 | Bhullar et al. |
| 6,413,410 B1 | 7/2002 | Hodges et al. |
| 6,420,128 B1 | 7/2002 | Ouyang et al. |
| 6,444,115 B1 | 9/2002 | Hodges et al. |
| 6,447,657 B1 | 9/2002 | Bhullar et al. |
| 6,454,921 B1 | 9/2002 | Hodges et al. |
| 6,461,496 B1 | 10/2002 | Feldman et al. |
| 6,475,360 B1 | 11/2002 | Hodges et al. |
| 6,475,372 B1 | 11/2002 | Ohara et al. |
| 6,484,046 B1 | 11/2002 | Say et al. |
| 6,485,923 B1 | 11/2002 | Yani et al. |
| 6,488,827 B1 | 12/2002 | Shartle |
| 6,489,133 B2 | 12/2002 | Phillips et al. |
| 6,491,803 B1 | 12/2002 | Shen et al. |
| 6,491,870 B2 | 12/2002 | Patel et al. |
| 6,501,976 B1 | 12/2002 | Sohrab |
| 6,503,381 B1 | 1/2003 | Gotoh et al. |
| 6,512,986 B1 | 1/2003 | Harmon |
| 6,514,718 B2 | 2/2003 | Heller et al. |
| 6,514,769 B2 | 2/2003 | Lee |
| 6,521,110 B1 | 2/2003 | Hodges et al. |
| 6,521,182 B1 | 2/2003 | Shartle et al. |
| 6,525,330 B2 | 2/2003 | Paolini et al. |
| 6,525,549 B1 | 2/2003 | Pollmann |
| 6,526,298 B1 | 2/2003 | Khalil et al. |
| 6,531,239 B2 | 3/2003 | Heller |
| 6,531,322 B1 | 3/2003 | Jurik et al. |
| 6,538,735 B1 | 3/2003 | Duebendorfer et al. |
| 6,540,890 B1 | 4/2003 | Bhullar et al. |
| 6,540,891 B1 | 4/2003 | Stewart et al. |
| 6,541,266 B2 | 4/2003 | Modzelewski et al. |
| 6,544,474 B2 | 4/2003 | Douglas |
| 6,549,796 B2 | 4/2003 | Sohrab |
| 6,551,494 B1 | 4/2003 | Heller et al. |
| 6,555,061 B1 | 4/2003 | Leong et al. |
| 6,558,528 B1 | 5/2003 | Matzinger |
| 6,560,471 B1 | 5/2003 | Heller et al. |
| 6,562,625 B2 | 5/2003 | Modzelewski et al. |
| 6,565,509 B1 | 5/2003 | Say et al. |
| 6,565,738 B1 | 5/2003 | Henning et al. |
| 6,570,390 B2 | 5/2003 | Hirayama et al. |
| 6,571,651 B1 | 6/2003 | Hodges |
| 6,572,822 B2 | 6/2003 | Jurik et al. |
| 6,574,425 B1 | 6/2003 | Weiss et al. |
| 6,576,101 B1 | 6/2003 | Heller et al. |
| 6,576,117 B1 | 6/2003 | Iketaki et al. |
| 6,576,416 B2 | 6/2003 | Haviland et al. |
| 6,576,461 B2 | 6/2003 | Heller et al. |
| 6,579,690 B1 | 6/2003 | Bonnecaze et al. |
| 6,591,125 B1 | 7/2003 | Buse et al. |
| 6,592,744 B1 | 7/2003 | Hodges et al. |
| 6,592,745 B1 | 7/2003 | Feldman et al. |
| 6,594,514 B2 | 7/2003 | Berner et al. |
| 6,599,406 B1 | 7/2003 | Kawanaka et al. |

| | | | | | | |
|---|---|---|---|---|---|---|
| 6,600,997 | B2 | 7/2003 | Deweese et al. | 2002/0168290 A1 | 11/2002 | Yuzhakov et al. |
| 6,605,200 | B1 | 8/2003 | Mao et al. | 2002/0168298 A1 | 11/2002 | Huhn et al. |
| 6,605,201 | B1 | 8/2003 | Mao et al. | 2002/0175075 A1 | 11/2002 | Deng et al. |
| 6,607,658 | B1 | 8/2003 | Heller et al. | 2002/0175087 A1 | 11/2002 | Hodges et al. |
| 6,616,819 | B1 | 9/2003 | Liamos et al. | 2002/0177788 A1 | 11/2002 | Hodges et al. |
| 6,618,934 | B1 | 9/2003 | Feldman et al. | 2002/0179440 A1 | 12/2002 | Tokunaga et al. |
| 6,623,501 | B2 | 9/2003 | Heller et al. | 2002/0179441 A1 | 12/2002 | Yamanishi et al. |
| 6,627,057 | B1 | 9/2003 | Bhullar et al. | 2002/0179442 A1 | 12/2002 | Miyazaki et al. |
| 6,632,349 | B1 | 10/2003 | Hodges et al. | 2002/0185385 A1 | 12/2002 | Charlton |
| 6,638,415 | B1 | 10/2003 | Hodges et al. | 2002/0189941 A1 | 12/2002 | Katsuki et al. |
| 6,638,716 | B2 | 10/2003 | Heller et al. | 2003/0000834 A1 | 1/2003 | Yoshioka et al. |
| 6,645,359 | B1 | 11/2003 | Bhullar et al. | 2003/0024811 A1 | 2/2003 | Davies et al. |
| 6,654,625 | B1 | 11/2003 | Say et al. | 2003/0032875 A1 | 2/2003 | Taniike et al. |
| 6,656,702 | B1 | 12/2003 | Yugawa et al. | 2003/0036202 A1 | 2/2003 | Teodorcyzk et al. |
| 6,662,439 | B1 * | 12/2003 | Bhullar ................. 29/825 | 2003/0042137 A1 | 3/2003 | Mao et al. |
| 6,676,995 | B2 | 1/2004 | Dick et al. | 2003/0042150 A1 | 3/2003 | Ryu et al. |
| 6,689,411 | B2 | 2/2004 | Dick et al. | 2003/0054427 A1 | 3/2003 | Phillips et al. |
| 6,814,844 | B2 | 11/2004 | Bhullar et al. | 2003/0064525 A1 | 4/2003 | Liess |
| 7,041,206 | B2 | 5/2006 | Gephart et al. | 2003/0073151 A1 | 4/2003 | Phillips et al. |
| 2001/0006149 | A1 | 7/2001 | Taniike et al. | 2003/0073152 A1 | 4/2003 | Phillips et al. |
| 2001/0006150 | A1 | 7/2001 | Taniike et al. | 2003/0073153 A1 | 4/2003 | Phillips et al. |
| 2001/0017269 | A1 | 8/2001 | Heller et al. | 2003/0079987 A1 | 5/2003 | Hodges et al. |
| 2001/0019831 | A1 | 9/2001 | Phillips et al. | 2003/0080001 A1 | 5/2003 | Hodges et al. |
| 2001/0034068 | A1 | 10/2001 | Spivey et al. | 2003/0088166 A1 | 5/2003 | Say et al. |
| 2001/0039057 | A1 | 11/2001 | Douglas et al. | 2003/0094383 A1 | 5/2003 | Kermani |
| 2001/0041830 | A1 | 11/2001 | Varalli et al. | 2003/0098233 A1 | 5/2003 | Kermani et al. |
| 2001/0042683 | A1 | 11/2001 | Musho et al. | 2003/0098234 A1 | 5/2003 | Hasegawa et al. |
| 2001/0052470 | A1 | 12/2001 | Hodges et al. | 2003/0100030 A1 | 5/2003 | Nadaoka et al. |
| 2001/0053535 | A1 | 12/2001 | Ladisch et al. | 2003/0100040 A1 | 5/2003 | Bonnecaze et al. |
| 2001/0054319 | A1 | 12/2001 | Heller et al. | 2003/0100821 A1 | 5/2003 | Heller et al. |
| 2001/0055784 | A1 | 12/2001 | Noda et al. | 2003/0102213 A1 | 6/2003 | Gotoh et al. |
| 2002/0003087 | A1 | 1/2002 | Chih-hui | 2003/0106809 A1 | 6/2003 | Kermani et al. |
| 2002/0004196 | A1 | 1/2002 | Whitson | 2003/0108976 A1 | 6/2003 | Braig et al. |
| 2002/0008038 | A1 | 1/2002 | Heller et al. | 2003/0109798 A1 | 6/2003 | Kermani |
| 2002/0019707 | A1 | 2/2002 | Cohen et al. | 2003/0132110 A1 | 7/2003 | Hasegawa et al. |
| 2002/0023489 | A1 | 2/2002 | Reimelt et al. | 2003/0134347 A1 | 7/2003 | Heller et al. |
| 2002/0025469 | A1 | 2/2002 | Heller | 2003/0143113 A2 | 7/2003 | Yuzhakov et al. |
| 2002/0029058 | A1 | 3/2002 | LeVaughn et al. | 2003/0143116 A1 | 7/2003 | Zheng et al. |
| 2002/0033345 | A1 | 3/2002 | Meade | 2003/0146110 A1 | 8/2003 | Karinka et al. |
| 2002/0040850 | A1 | 4/2002 | Liu et al. | 2003/0150724 A1 | 8/2003 | Kawanaka et al. |
| 2002/0042090 | A1 | 4/2002 | Heller et al. | 2003/0152823 A1 | 8/2003 | Heller |
| 2002/0043471 | A1 | 4/2002 | Ikeda et al. | 2003/0155237 A1 | 8/2003 | Surridge et al. |
| 2002/0044890 | A1 | 4/2002 | Black | 2003/0155538 A1 | 8/2003 | Siepmann |
| 2002/0053523 | A1 | 5/2002 | Liamos et al. | 2003/0159944 A1 | 8/2003 | Pottgen et al. |
| 2002/0081588 | A1 | 6/2002 | De Lumley-woodyear et al. | 2003/0159945 A1 | 8/2003 | Miyazaki et al. |
| 2002/0082797 | A1 | 6/2002 | Deweese et al. | 2003/0164293 A1 | 9/2003 | Hodges et al. |
| 2002/0084184 | A1 | 7/2002 | Chambers et al. | 2003/0167862 A1 | 9/2003 | Hodges |
| 2002/0084196 | A1 | 7/2002 | Liamos et al. | 2003/0168338 A1 | 9/2003 | Gao et al. |
| 2002/0092612 | A1 | 7/2002 | Davies et al. | 2003/0175841 A1 | 9/2003 | Watanabe et al. |
| 2002/0100685 | A1 | 8/2002 | Huang et al. | 2003/0175946 A1 | 9/2003 | Tokunaga et al. |
| 2002/0102739 | A1 | 8/2002 | Nomura et al. | 2003/0176183 A1 | 9/2003 | Drucker et al. |
| 2002/0112969 | A1 | 8/2002 | Hodges et al. | 2003/0178322 A1 | 9/2003 | Iyengar et al. |
| 2002/0117404 | A1 | 8/2002 | Maxwell et al. | 2003/0179914 A1 | 9/2003 | Tokunaga |
| 2002/0117639 | A1 | 8/2002 | Paolini et al. | 2003/0180183 A1 | 9/2003 | Fukuoka et al. |
| 2002/0125145 | A1 | 9/2002 | Ohara et al. | 2003/0187338 A1 | 10/2003 | Say et al. |
| 2002/0130042 | A1 | 9/2002 | Moerman et al. | 2003/0188427 A1 | 10/2003 | Say et al. |
| 2002/0130043 | A1 | 9/2002 | Hodges et al. | 2003/0190069 A1 | 10/2003 | Nikitin et al. |
| 2002/0133064 | A1 | 9/2002 | Ueno et al. | 2003/0199744 A1 | 10/2003 | Buse et al. |
| 2002/0137200 | A1 | 9/2002 | Takahashi et al. | 2003/0199893 A1 | 10/2003 | Boecker et al. |
| 2002/0137230 | A1 | 9/2002 | Nadaoka et al. | 2003/0201194 A1 | 10/2003 | Heller et al. |
| 2002/0138275 | A1 | 9/2002 | Amano et al. | 2003/0203498 A1 | 10/2003 | Neel et al. |
| 2002/0138356 | A1 | 9/2002 | Dutta et al. | 2003/0203503 A1 | 10/2003 | Fukuoka et al. |
| 2002/0139692 | A1 | 10/2002 | Tokunaga et al. | 2003/0217918 A1 | 11/2003 | Davies et al. |
| 2002/0146835 | A1 | 10/2002 | Modzelewski et al. | 2004/0005721 A1 | 1/2004 | Tanike et al. |
| 2002/0148726 | A1 | 10/2002 | Yamamoto et al. | 2004/0016642 A1 | 1/2004 | Miyazaki et al. |
| 2002/0148739 | A2 | 10/2002 | Liamos et al. | 2004/0020777 A1 | 2/2004 | Miyamoto et al. |
| 2002/0150930 | A1 | 10/2002 | Nadaoka et al. | 2004/0106941 A1 | 6/2004 | Roe et al. |
| 2002/0152793 | A1 | 10/2002 | Sato et al. | 2004/0256248 A1 | 12/2004 | Burke et al. |
| 2002/0155030 | A1 | 10/2002 | Matsuda et al. | | | |
| 2002/0155615 | A1 | 10/2002 | Novikov et al. | | | |
| 2002/0157948 | A2 | 10/2002 | Liamos et al. | | | |

FOREIGN PATENT DOCUMENTS

| | | | | | | |
|---|---|---|---|---|---|---|
| 2002/0160517 | A1 | 10/2002 | Modzelewski et al. | DE | 36 43 263 | 7/1988 |
| 2002/0164822 | A1 | 11/2002 | Takahashi et al. | DE | 40 11 428 A1 | 11/1990 |

| | | | | | | |
|---|---|---|---|---|---|---|
| DE | 298 14 997 U1 | 8/1993 | | EP | 1 324 038 | 7/2003 |
| DE | 199 36 693 | 2/2001 | | EP | 1 327 881 | 7/2003 |
| EP | 0 010 456 | 4/1980 | | EP | 1 352 611 A1 | 10/2003 |
| EP | 0 034 049 | 8/1981 | | EP | 1 352 969 | 10/2003 |
| EP | 0 057 110 | 8/1982 | | EP | 1 369 684 | 12/2003 |
| EP | 0 073 056 A2 | 3/1983 | | EP | 1 369 687 | 12/2003 |
| EP | 0 084 874 A1 | 8/1983 | | EP | 1 119 637 | 3/2004 |
| EP | 0 101 880 | 3/1984 | | EP | 1 394 535 | 3/2004 |
| EP | 0 132 790 A2 | 2/1985 | | EP | 1 413 879 | 4/2004 |
| EP | 0 164 180 | 12/1985 | | EP | 1 431 758 A1 | 6/2004 |
| EP | 0 171 148 | 2/1986 | | GB | 2 295 676 | 6/1996 |
| EP | 0 171 239 | 2/1986 | | GB | 2 365 123 | 2/2002 |
| EP | 0 186 286 | 7/1986 | | JP | 63-111453 | 5/1988 |
| EP | 0 241 309 A2 | 10/1987 | | JP | 63-128252 | 5/1988 |
| EP | 0 287 883 | 10/1988 | | JP | 01-291153 | 11/1989 |
| EP | 0 359 831 | 3/1990 | | JP | 03-099254 | 4/1991 |
| EP | 0 206 218 B1 | 6/1991 | | JP | 04-121652 | 4/1992 |
| EP | 0 471 986 A2 | 2/1992 | | JP | 93-312761 | 11/1993 |
| EP | 0 471 986 A3 | 4/1992 | | JP | 08-262026 | 10/1996 |
| EP | 0 255 291 B1 | 6/1992 | | JP | 09-043242 | 2/1997 |
| EP | 0 546 536 | 6/1993 | | JP | 91-59644 | 6/1997 |
| EP | 0 244 326 B1 | 8/1993 | | JP | 10 332626 | 12/1998 |
| EP | 0 537 761 A3 | 2/1994 | | JP | 2000-19146 | 1/2000 |
| EP | 0 417 796 B1 | 11/1994 | | JP | 2000 019147 | 1/2000 |
| EP | 0 213 343 B2 | 2/1995 | | RU | 2180514 | 3/2002 |
| EP | 0 636 880 A2 | 2/1995 | | WO | WO 81/01794 | 7/1981 |
| EP | 0 640 832 | 3/1995 | | WO | WO 83/00926 | 3/1983 |
| EP | 0 651 250 A2 | 5/1995 | | WO | WO 86/07632 | 12/1986 |
| EP | 0 471 986 B1 | 10/1995 | | WO | WO 89/08713 | 9/1989 |
| EP | 0 127 958 B2 | 4/1996 | | WO | WO 89/09397 | 10/1989 |
| EP | 0 732 406 A1 | 9/1996 | | WO | WO 90/05293 | 5/1990 |
| EP | 0 732 590 A2 | 9/1996 | | WO | WO 92/01928 | 2/1992 |
| EP | 0 383 322 B1 | 2/1997 | | WO | WO 92/07655 | 5/1992 |
| EP | 0 537 761 B1 | 8/1997 | | WO | WO 92/15859 | 9/1992 |
| EP | 0 837 320 A3 | 4/1998 | | WO | WO 92/15861 | 9/1992 |
| EP | 0 840 122 A2 | 5/1998 | | WO | WO 92/15950 | 9/1992 |
| EP | 0 851 224 | 7/1998 | | WO | WO 92/22669 | 12/1992 |
| EP | 0 859 230 | 8/1998 | | WO | WO 93/09433 | 5/1993 |
| EP | 0 878 713 | 11/1998 | | WO | WO 94/12950 | 6/1994 |
| EP | 0 887 421 A1 | 12/1998 | | WO | WO 94/16095 | 7/1994 |
| EP | 0 894 509 A2 | 2/1999 | | WO | WO 94/23295 | 10/1994 |
| EP | 0 470 649 B1 | 6/1999 | | WO | WO 94/28414 | 12/1994 |
| EP | 0 942 278 A2 | 9/1999 | | WO | WO 94/29705 | 12/1994 |
| EP | 0 964 059 | 12/1999 | | WO | WO 95/03542 | 2/1995 |
| EP | 0 987 544 | 3/2000 | | WO | WO 95/06919 | 3/1995 |
| EP | 1 024 358 A1 | 8/2000 | | WO | WO 95/07050 | 3/1995 |
| EP | 1 035 216 A1 | 9/2000 | | WO | WO 95/22597 | 8/1995 |
| EP | 0 230 472 B2 | 12/2000 | | WO | WO 96/04398 | 2/1996 |
| EP | 1 067 384 A2 | 1/2001 | | WO | WO 96/07908 | 3/1996 |
| EP | 1 074 832 A1 | 2/2001 | | WO | WO 96/13707 | 5/1996 |
| EP | 1 081 490 A1 | 3/2001 | | WO | WO 96/15454 | 5/1996 |
| EP | 1 130 390 A1 | 9/2001 | | WO | WO 96/33403 | 10/1996 |
| EP | 0 741 186 B1 | 10/2001 | | WO | WO 97/00441 | 1/1997 |
| EP | 1 143 245 | 10/2001 | | WO | WO 97/02487 | 1/1997 |
| EP | 1 147 739 A2 | 10/2001 | | WO | WO 97/08544 | 3/1997 |
| EP | 1 152 239 A1 | 11/2001 | | WO | WO 97/16726 | 5/1997 |
| EP | 1 156 324 | 11/2001 | | WO | WO 97/18465 | 5/1997 |
| EP | 1 225 448 | 7/2002 | | WO | WO 97/29366 | 8/1997 |
| EP | 1 235 069 A1 | 8/2002 | | WO | WO 97/29847 | 8/1997 |
| EP | 0 958 495 | 11/2002 | | WO | WO 97/30344 | 8/1997 |
| EP | 1 102 991 B1 | 11/2002 | | WO | WO 97/39341 | 10/1997 |
| EP | 1 256 798 | 11/2002 | | WO | WO 97/39343 | 10/1997 |
| EP | 1 275 732 | 1/2003 | | WO | WO 97/42882 | 11/1997 |
| EP | 1 281 955 | 2/2003 | | WO | WO 97/42888 | 11/1997 |
| EP | 1 009 850 B1 | 3/2003 | | WO | WO 97/45719 | 12/1997 |
| EP | 1 288 653 A1 | 3/2003 | | WO | WO 98/05424 | 2/1998 |
| EP | 1 312 919 A2 | 5/2003 | | WO | WO 98/19153 | 5/1998 |
| EP | 1 316 367 | 6/2003 | | WO | WO 98/19159 | 5/1998 |
| EP | 1 318 396 A1 | 6/2003 | | WO | WO 98/29740 | 7/1998 |
| EP | 0 876 506 | 7/2003 | | WO | WO 98/35225 | 8/1998 |
| EP | 1 129 211 B1 | 7/2003 | | WO | WO 98/55853 | 12/1998 |
| EP | 1 308 720 A1 | 7/2003 | | WO | WO 98/57159 | 12/1998 |
| EP | 1 324 025 A2 | 7/2003 | | WO | WO 99/05966 | 2/1999 |

| | | |
|---|---|---|
| WO | WO 99/09404 | 2/1999 |
| WO | WO 99/12008 | 3/1999 |
| WO | WO 99/12021 | 3/1999 |
| WO | WO 99/13099 | 3/1999 |
| WO | WO 99/13100 | 3/1999 |
| WO | WO 99/05516 | 4/1999 |
| WO | WO 99/22236 | 5/1999 |
| WO | WO 99/23479 | 5/1999 |
| WO | WO 99/29230 | 6/1999 |
| WO | WO 99/30152 | 6/1999 |
| WO | WO 99/32881 | 7/1999 |
| WO | WO 99/39627 | 8/1999 |
| WO | WO 99/41596 | 8/1999 |
| WO | WO 99/51974 | 10/1999 |
| WO | WO 99/57317 | 11/1999 |
| WO | WO 99/58709 | 11/1999 |
| WO | WO 99/59464 | 11/1999 |
| WO | WO 99/60383 | 11/1999 |
| WO | WO 99/64620 | 12/1999 |
| WO | WO 00/09996 | 2/2000 |
| WO | WO 00/10007 | 2/2000 |
| WO | WO 00/20626 | 4/2000 |
| WO | WO 00/26638 | 5/2000 |
| WO | WO 00/28068 | 5/2000 |
| WO | WO 00/33072 | 6/2000 |
| WO | WO 00/33074 | 6/2000 |
| WO | WO 00/42422 | 7/2000 |
| WO | WO 00/45160 | 8/2000 |
| WO | WO 00/54047 | 9/2000 |
| WO | WO 00/57177 | 9/2000 |
| WO | WO 00/60340 | 10/2000 |
| WO | WO 00/62047 | 10/2000 |
| WO | WO 00/73778 | 12/2000 |
| WO | WO 00/73785 A2 | 12/2000 |
| WO | WO 00/78917 A1 | 12/2000 |
| WO | WO 00/78992 | 12/2000 |
| WO | WO 01/02093 A2 | 1/2001 |
| WO | WO 01/13115 A2 | 2/2001 |
| WO | WO 01/13115 A3 | 2/2001 |
| WO | WO 01/25775 | 4/2001 |
| WO | WO 01/25776 | 4/2001 |
| WO | WO 01/28423 | 4/2001 |
| WO | WO 01/73420 A1 | 4/2001 |
| WO | WO 01/30915 | 5/2001 |
| WO | WO 01/33216 A1 | 5/2001 |
| WO | WO 01/36430 | 5/2001 |
| WO | WO 01/36660 | 5/2001 |
| WO | WO 01/36953 A1 | 5/2001 |
| WO | WO 01/46457 A2 | 6/2001 |
| WO | WO 01/40788 | 7/2001 |
| WO | WO 01/57238 | 8/2001 |
| WO | WO 01/57239 | 8/2001 |
| WO | WO 01/57510 | 8/2001 |
| WO | WO 01/64105 | 9/2001 |
| WO | WO 01/67099 A1 | 9/2001 |
| WO | WO 01/71328 A1 | 9/2001 |
| WO | WO 01/71329 | 9/2001 |
| WO | WO 01/72220 | 10/2001 |
| WO | WO 01/73109 | 10/2001 |
| WO | WO 01/73114 | 10/2001 |
| WO | WO 01/73124 | 10/2001 |
| WO | WO 01/73395 | 10/2001 |
| WO | WO 01/74242 | 10/2001 |
| WO | WO 01/75433 | 10/2001 |
| WO | WO 01/75438 A2 | 10/2001 |
| WO | WO 01/84133 A1 | 11/2001 |
| WO | WO 01/84142 | 11/2001 |
| WO | WO 01/88524 | 11/2001 |
| WO | WO 01/92857 | 12/2001 |
| WO | WO 01/95806 | 12/2001 |
| WO | WO 01/96596 | 12/2001 |
| WO | WO 02/00112 A2 | 1/2002 |
| WO | WO 02/06822 | 1/2002 |
| WO | WO 02/08750 | 1/2002 |
| WO | WO 02/08753 A2 | 1/2002 |
| WO | WO 02/10728 | 2/2002 |
| WO | WO 02/13966 | 2/2002 |
| WO | WO 02/13970 | 2/2002 |
| WO | WO 02/14535 | 2/2002 |
| WO | WO 02/18053 A1 | 3/2002 |
| WO | WO 02/22855 | 3/2002 |
| WO | WO 02/32559 | 4/2002 |
| WO | WO 02/48707 | 6/2002 |
| WO | WO 02/49507 | 6/2002 |
| WO | WO 02/50609 | 6/2002 |
| WO | WO 02/054055 A1 | 7/2002 |
| WO | WO 02/057767 A1 | 7/2002 |
| WO | WO 02/057768 A | 7/2002 |
| WO | WO 02/057781 | 7/2002 |
| WO | WO 02/058537 | 8/2002 |
| WO | WO 02/062212 | 8/2002 |
| WO | WO 02/067768 | 9/2002 |
| WO | WO 02/070734 A1 | 9/2002 |
| WO | WO 02/071044 | 9/2002 |
| WO | WO 02/078512 A2 | 10/2002 |
| WO | WO 02/078533 | 10/2002 |
| WO | WO 02/086483 | 10/2002 |
| WO | WO 02/093152 | 11/2002 |
| WO | WO 02/095355 | 11/2002 |
| WO | WO 02/097418 | 12/2002 |
| WO | WO 02/103343 A1 | 12/2002 |
| WO | WO 03/005015 | 1/2003 |
| WO | WO 03/012422 | 2/2003 |
| WO | WO 03/014740 A1 | 2/2003 |
| WO | WO 03/014741 A1 | 2/2003 |
| WO | WO 03/015627 | 2/2003 |
| WO | WO 03/015629 | 2/2003 |
| WO | WO 03/021706 A1 | 3/2003 |
| WO | WO 03/025257 | 3/2003 |
| WO | WO 03/029804 | 4/2003 |
| WO | WO 03/032411 | 4/2003 |
| WO | WO 03/039483 A2 | 5/2003 |
| WO | WO 03/042679 A1 | 5/2003 |
| WO | WO 03/042680 A1 | 5/2003 |
| WO | WO 03/044513 | 5/2003 |
| WO | WO 03/048756 A1 | 6/2003 |
| WO | WO 03/060154 A2 | 7/2003 |
| WO | WO 03/067252 | 8/2003 |
| WO | WO 03/069304 A2 | 8/2003 |
| WO | WO 03/083469 | 10/2003 |
| WO | WO 03/085372 | 10/2003 |
| WO | WO 03/091717 | 11/2003 |
| WO | WO 2004/005908 | 1/2004 |
| WO | 2005124331 A1 | 12/2005 |

OTHER PUBLICATIONS

Aoki et al., "Time-Dependence Of Diffusion-Controlled Currents Of A Soluble Redox Couple At Interdigitated Microarray Electrodes". J. Electroanal. Chem. 266 (1989) 11-20.

Bartlett, P.N. and Whitaker, R.G., "Electrochemical Immobilisation of Enzymes: Part I. Theory", J. Electroanal Chem., 224 (1987) 27-35.

Bartlett, P.N. and Whitaker, R.G., "Electrochemical Immobilisation of Enzymes: Part II. Glucose Oxidase Immobilised In Poly-N-Methylpyrrole", J. Electroanal. Chem., 224 (1987) 37-48.

Beyer et al., "Development and Application of a New Enzyme Sensor Type Based on the EIS-Capacitance Structure for Bioprocess Control," Biosensors & Bioelectronics, vol. 9, pp. 17-21 (1994).

Bradley et al., "Kinetic Analysis of Enzyme Electrode Response," Anal. Chem., vol. 56, pp. 664-667 (1984).

Burke, et al., Improved-Accuracy Biosensor Strip For AccuChek™ Advantage®, Presented Orally At ACS Boston Meeting (~1993-1994).

Cardosi et al., " The Realization of Electron Transfer from Biological Molecules to Electrodes, " Biosensors Fundamentals and Applications, chapt. 15 (Turner et al. eds., Oxford University Press. 1987).

Cass et al., "Ferrocene-Mediated Enzyme Electrode for Amperometric Determination of Glucose," Anal. Chem, vol. 56, pp. 667-671 (1984).

Chiba, K.; Ohsaka, T.; Ohnuki, Y.; and Oyama, N., "Electrochemical Preparation of A Ladder Polymer Containing Phenazine Rings." J. Eleectroanal Chemo., 219 (1987) 117-124.

Gebhardt, et al., "Electrocatalytic Glucose Sensor," Siemens Forsch-u, Entwickl-Ber. Bd., vol. 12, pp. 91-95 (1983).

Gregg, et al., "Cross-Lined Redox Gels Containing Glucose Oxidase For Amperometric Biosensor Applications", Anal. Chem. 1990, 62, 258-263.

Hintsche, R. et al., "Chip Biosensors On Thin-Film Metal Electrodes", Sensors and Actuators B. 4 (1991) 287-291.

Ho et al., "Electrochemical Sensor for Measurement of Urea and Creatinine in Serum Based on AC Impedance Measurement of Enzyme-Catalyzed Polymer Transformation." Analytical Chemistry, vol. 71, No. 10, May 15, 1999.

Jin et al., "Application Of The Finite Analytic Numerical Method. Part 1. Diffusion Problems On Coplanar an dElevated Interdigitated Microarray Band Electrodes" J. Electroanal. Chem. 441 (1996) 29-36.

Kasapbasioglu et al., "An Impedance Based Ultra-Thin Platinum Island Film Glucose Sensor," Sensor and Actuators B. vol. 13-14, pp. 749-451 (1993).

Koichi, "Measurements of Current-Potential Curves, 6, Cottrell Equation and its Analogs. What Can We Know from Chronoamperometry?" Denki Kagaku ovopi Kogyo Butsuri Kagaku, vol. 54, No. 6, pp. 471-475 (1986).

Lambda Physik Brochure For LPX® Series.

Lee, et al., "A New Glucose Sensor Using Microporous Enzyme Membrane", Sensors and Actuators B, 3 (1991) 215-219.

Lifescan Guide Entitled "Quick Start" For The Onetouch® Ultra™ Blood Glucose Monitoring System.

Lifescan Owner's Booklet Entitled "The Comfort of Control".

Lifescan Product Brochure For Onetouch® Ultra™ Blood Glucose Monitoring System.

Lifescan Product Brochure For Onetouch® Ultra™ Test Strip.

Malitesta, et al., "Glucose Fast-Response Amperometric Sensor Based On Glucose Oxidase Immobilized In An Electpolymerized Poly (O-Phenylenediamine) Film", Anal. Chem. 1990, 62, 2735-2740.

Meier, et al., "Sensor and Sensor Elements Manufacturing: Laser Direct Patterning (LDP) for Reel to Reel Processing to generate High Throughput", LPKF Laser & Electronics AG, pp. 1-6.

Mell, et al., "A Model for the Amperometric Enzyme Electrode Obtained Through Digital Simulation and Applied to the immobilized Glucose Oxidase System," Analytical Chemistry, vol. 37, pp. 299-307 (Feb. 1975).

Mell et al., "Amperometric Response Enhancement of the Immobilized Glucose Oxidase Enzyme Electrode", Analytical Chemistry, vol. 48, pp. 1597-1601 (Sep. 1976).

Miao et al., "Amperometric Glucose Biosensor Based On Immobilization of Glucose Oxidase In Chitosan dMartrix Cross-Linked With Glutaraldehyde", Electroanalysis 2001, 13, No. 4, 347-349.

Mohri, et al., "Characteristic Response of Electrochemical Nonlinearity to Taste Compounds with a Gold Electrode Modified with 4-Aminobenzenethiol," Bull, Chem. Soc. Jon., vol. 66, pp. 1328-1332 (1993).

Morris, et al., "An Electrochemical Capillary Fill Device for the Analysis of Glucose Incorporating Glucose Oxidase and Ruthenium (III) Hexamine as Mediator," Electroanalysis, vol. 4, pp. 1-9 (1992).

Muller et al., "Influence of Hematocrit and Platelet Count on Impedance and Reactivity of Whole Blood for Electrical Aggregometry," Journal of Pharmacological and Toxicological Methods, vol. 34, pp. 17-22 (1995).

Myland et al., "Membrane-Covered Oxygen Sensors: An Exact Treatment of the Switch-on Transient," Journal of the Electrochemical Society, vol. 131, pp. 1815-1823 (Aug. 1984).

Nishihara et al., "Interdigitated Array Electrode Diffusion Measurements in Donor/Acceptor Solutions in Polyether Electrolyte Solvents", Anal. Chem. 1991, 63, 2955-2960.

Niwa et al., "Electrochemical Behavior Of Reversible Redox Species At Interdigitated Array Electrodes With Different Geometries: Consideration Of Redox Cycling and Collection Efficiency" Anal. Chem. 62 (1990) 447-452.

Paeschke et al., "Properties of Interdigital Electrode Arrays With Different Geometries", Analytica Chimica Acta 305 (1995) 126-136.

Preidel et al. "Glucose Measurements by Electrocatalytic Sensor in the Extracorporeal Blood Circulation of a Sheep," Sensors and Actuators B, vol. 2, pp. 257-263 (1990).

Preidel et al. "In Vitro Measurements with Electrocatalytic Glucose Sensor in Blood," Biomed. Biochim. Acta, vol. 48, pp. 897-903 (1989).

Saeger et al., "Influence of Urea on the Glucose Measurement by Electrocatalytic Sensor in the Extracorporeal Blood Circulation of a Sheep," Biomed. Biochim. Acta, vol. 50, pp. 885-891 (1991).

Skladal, "Compensation of Temperature Variations Disturbing Performance of an Amperometric Biosensor for Continuous Monitoring," Sensors and Actuators B, Elsevier Sequoia S.A., Lausanne, CH, vol. 28, No. 1, Jul. 1, 1995, pp. 59-62, XP004004390, ISSN: 0925-4005.

Talbott, et al., "A New Microchemical Approach to Amperometric Analysis," Microchemical Journal, vol. 37, pp. 5-12 (1988).

Tender et al., "Electrochemical Patterning of Self-Assembled Monolayers onto Microscopic Arrays of Gold Electrodes Fabricated by Laser Ablation," American Chemical Society, Langmuir, vol. 12, No. 23, pp. 5515-5518, (1996).

Vorburger et al., "In the Rough," National Institute of Standards and Technology, and Ndubuisi Orji, University of North Carolina, Spie's oe magazine, pp. 31-34, (2002).

Williams et al., "Electrochemical-Enzymatic Analysis of Blood Glucose and Lactate." Analytical Chemistry, vol. 42, No. 1, pp. 118-121 (Jan. 1970).

Wollenberger et al., "Interdigitated Array Microelectrodes For The Determination Of Enzyme Activities", Analyst, Jun. 1994, 1245-1249.

Zhao, "Contributions of Suspending Medium to Electrical Impedance of Blood," Biochimica et Biophysica Acta, vol. 1201, pp. 179-185 (1994).

Zhao, "Electrical Impedance and Haematocrit of Human Blood with Various Anticoagulants," Physiol. Meas., vol. 14, pp. 299-307 (1993).

http://216.239.41.104/search?q=cache:oNNpSzoOXvgJ:www.future-fab.com, "Introduction", Future Fab International, Montgomery Research, Inc., pp. 1-10, (Jan. 2004).

http://216.239.41.104/search?q=cache:bEmigilMhtUJ:www.coe.uncc.edu, "LER", Ndubuisi George Orji, pp. 1-3 (Jan. 2004).

http://www.circuittree.com, Vaucher et al., "Laser Direct Imaging and Structuring: An Update", posted on Aug. 2002, pp. 1-6 (Nov. 2003).

http://www.ifm.liu.se/Applphys/ftir/sams.html, "Self-Assembled Monolayers", pp. 1-5 (Jan. 2004).

http://www.tamsci.com/library/news-05-DECEMBER-2002.html, "Patterning Thin Film Circuits at the Speed of Light", Press Release, pp. 1-2 (Nov. 2003).

http://www.zurich.ibm.com/~bmi/samtech.html, "Technological Application of Self-Assembled Monolayers", pp. 1-2 (Jan. 2004).

US 6,517,703, 02/2003, Beaty et al. (withdrawn)

* cited by examiner

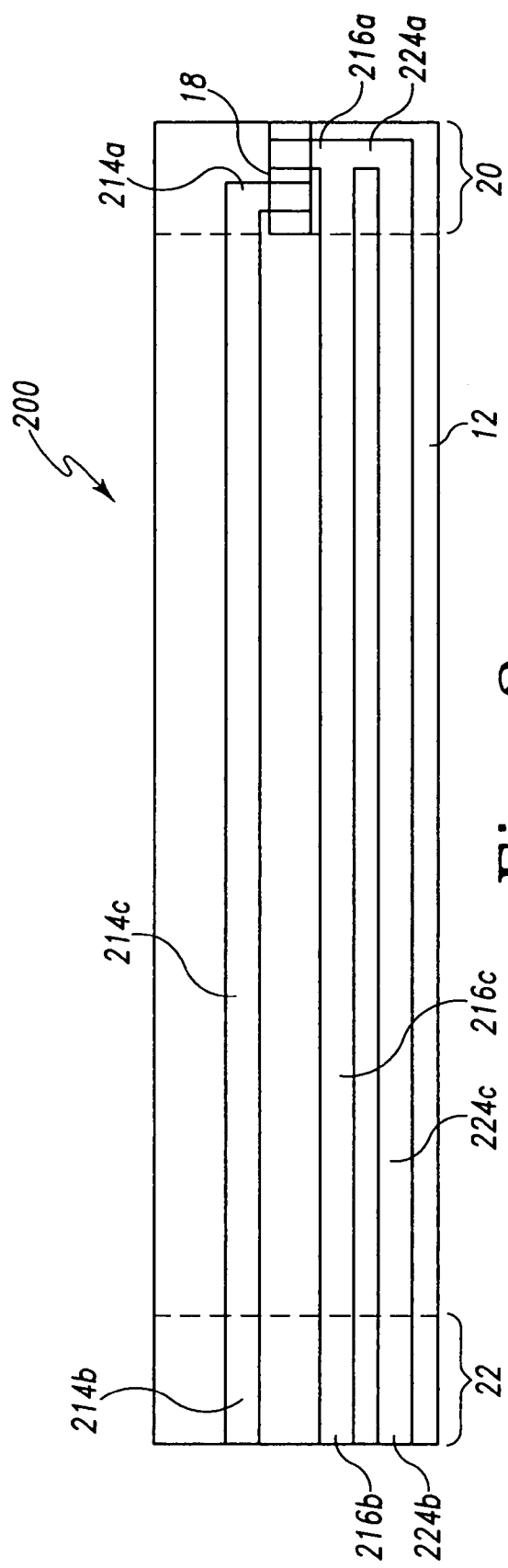
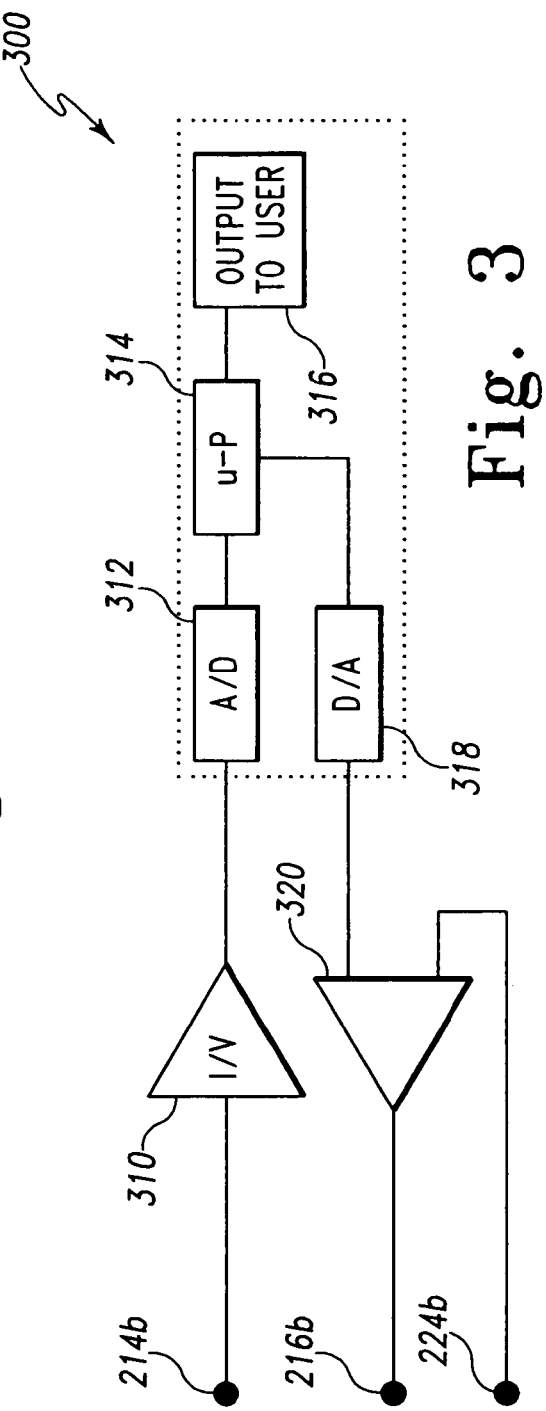

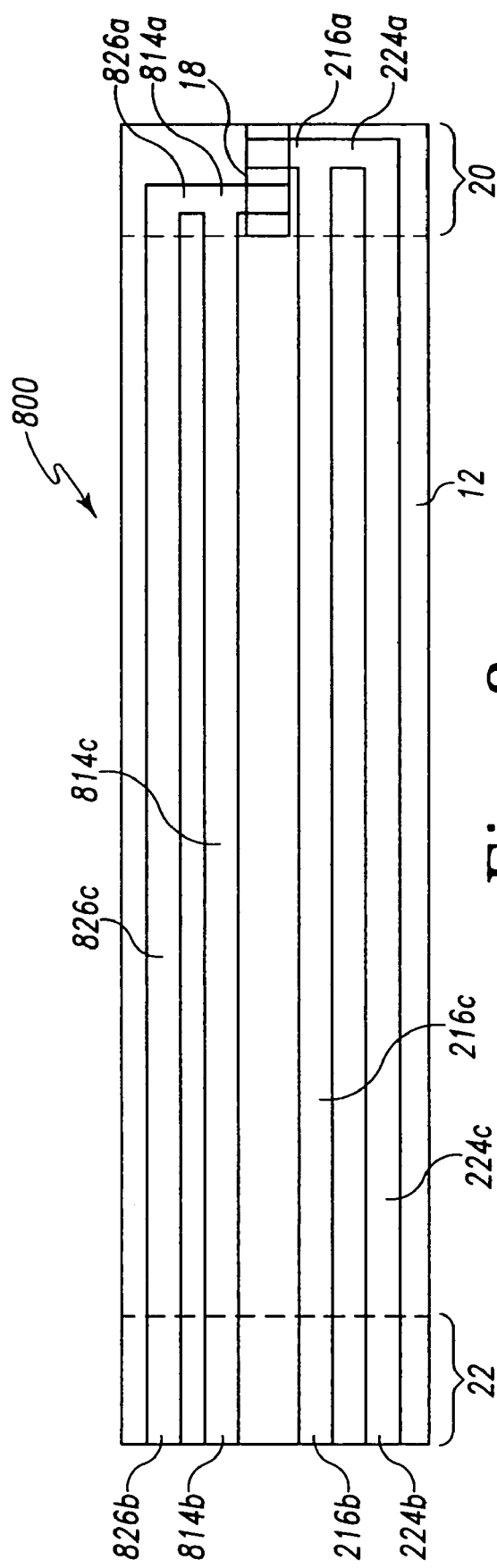
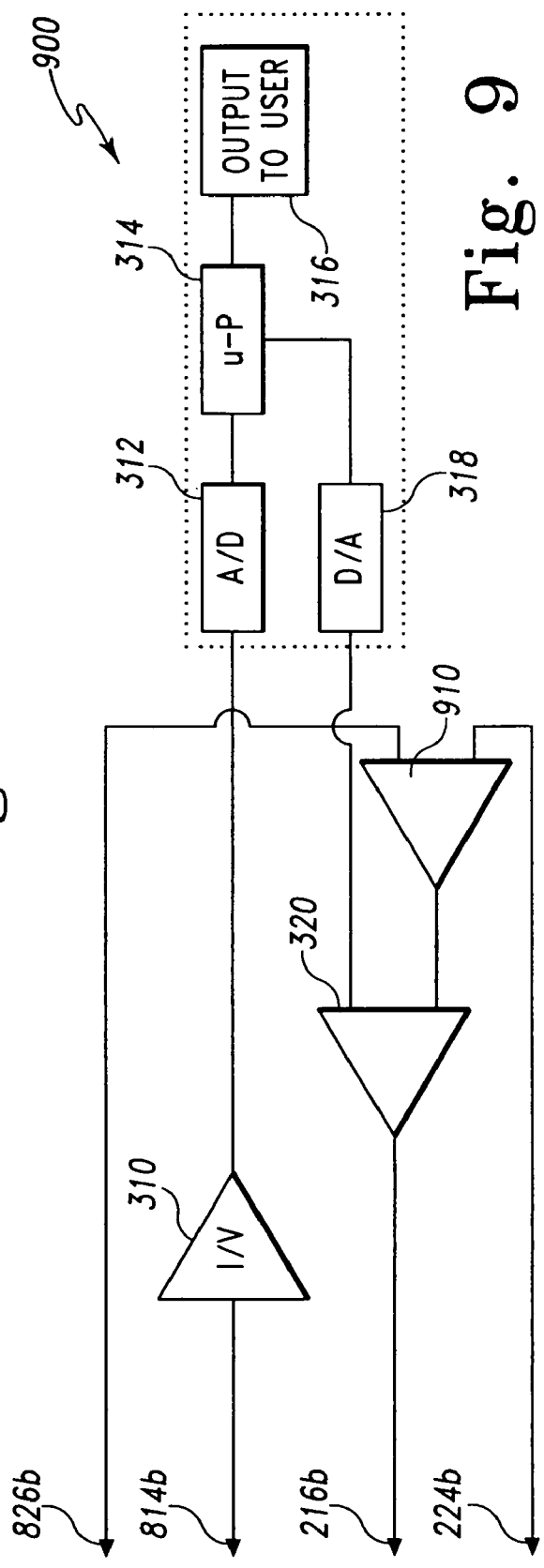

US 7,556,723 B2

ELECTRODE DESIGN FOR BIOSENSOR

REFERENCE TO RELATED APPLICATIONS

This application claims the benefit of U.S. Provisional Application No. 60/581,002, filed Jun. 18, 2004. This application is a continuation-in-part of prior application Ser. No. 10/961,352, now abandoned, filed Oct. 8, 2004 entitled "SYSTEM AND METHOD FOR QUALITY ASSURANCE OF A BIOSENSOR TEST STRIP." This application is also related to application Ser. No. 10/871,937 filed Jun. 18, 2004, and which is incorporated herein by reference in its entirety.

TECHNICAL FIELD

The present invention relates to an apparatus for use in measuring signals such as those related to concentrations of an analyte (such as blood glucose) in a biological fluid as well as those related to interferants (such as hematocrit and temperature in the case of blood glucose) to analyte concentration signals. The invention relates more particularly to a system and method for quality assurance of a biosensor test strip.

BACKGROUND

Measuring the concentration of substances in biological fluids is an important tool for the diagnosis and treatment of many medical conditions. For example, the measurement of glucose in body fluids, such as blood, is crucial to the effective treatment of diabetes.

Diabetic therapy typically involves two types of insulin treatment: basal, and meal-time. Basal insulin refers to continuous, e.g. time-released insulin, often taken before bed. Meal-time insulin treatment provides additional doses of faster acting insulin to regulate fluctuations in blood glucose caused by a variety of factors, including the metabolization of sugars and carbohydrates. Proper regulation of blood glucose fluctuations requires accurate measurement of the concentration of glucose in the blood. Failure to do so can produce extreme complications, including blindness and loss of circulation in the extremities, which can ultimately deprive the diabetic of use of his or her fingers, hands, feet, etc.

Multiple methods are known for determining the concentration of analytes in a blood sample, such as, for example, glucose. Such methods typically fall into one of two categories: optical methods and electrochemical methods. Optical methods generally involve spectroscopy to observe the spectrum shift in the fluid caused by concentration of the analyte, typically in conjunction with a reagent that produces a known color when combined with the analyte. Electrochemical methods generally rely upon the correlation between a current (Amperometry), a potential (Potentiometry) or accumulated charge (Coulometry) and the concentration of the analyte, typically in conjunction with a reagent that produces charge-carriers when combined with the analyte. See, for example, U.S. Pat. No. 4,233,029 to Columbus, U.S. Pat. No. 4,225,410 to Pace, U.S. Pat. No. 4,323,536 to Columbus, U.S. Pat. No. 4,008,448 to Muggli, U.S. Pat. No. 4,654,197 to Lilja et al., U.S. Pat. No. 5,108,564 to Szuminsky et al., U.S. Pat. No. 5,120,420 to Nankai et al., U.S. Pat. No. 5,128,015 to Szuminsky et al., U.S. Pat. No. 5,243,516 to White, U.S. Pat. No. 5,437,999 to Diebold et al., U.S. Pat. No. 5,288,636 to Pollmann et al., U.S. Pat. No. 5,628,890 to Carter et al., U.S. Pat. No. 5,682,884 to Hill et al., U.S. Pat. No. 5,727,548 to Hill et al., U.S. Pat. No. 5,997,817 to Crismore et al., U.S. Pat. No. 6,004,441 to Fujiwara et al., U.S. Pat. No. 4,919,770 to Priedel, et al., and U.S. Pat. No. 6,054,039 to Shieh, which are hereby incorporated in their entireties. The biosensor for conducting the tests is typically a disposable test strip having a reagent thereon that chemically reacts with the analyte of interest in the biological fluid. The test strip is mated to a nondisposable test meter such that the test meter can measure the reaction between the analyte and the reagent in order to determine and display the concentration of the analyte to the user.

FIG. 1 schematically illustrates a typical prior art disposable biosensor test strip, indicated generally at 10 (see, for example, U.S. Pat. Nos. 4,999,582 and 5,438,271, assigned to the same assignee as the present application, and incorporated herein by reference). The test strip 10 is formed on a nonconductive substrate 12, onto which are formed conductive areas 14,16. A chemical reagent 18 is applied over the conductive areas 14,16 at one end of the test strip 10. The reagent 18 will react with the analyte of interest in the biological sample in a way that can be detected when a voltage potential is applied between the measurement electrodes 14a and 16a.

The test strip 10 therefore has a reaction zone 20 containing the measurement electrodes 14a,16a that comes into direct contact with a sample that contains an analyte for which the concentration in the sample is to be determined. In an amperometric or coulometric electrochemical measurement system, the measurement electrodes 14a,16a in the reaction zone 20 are coupled to electronic circuitry (typically in a test meter (not shown) into which the test strip 10 is inserted, as is well known in the art) that supplies an electrical potential to the measurement electrodes and measures the response of the electrochemical sensor to this potential (e.g. current, impedance, charge, etc.). This response is proportional to the analyte concentration.

The test meter contacts the test strip 10 at contact pads 14b,16b in a contact zone 22 of the test strip 10. Contact zone 22 is located somewhat remotely from measurement zone 20, usually (but not always) at an opposite end of the test strip 10. Conductive traces 14c,16c couple the contact pads 14b,16b in the contact zone 22 to the respective measurement electrodes 14a,16a in the reaction zone 20.

Especially for biosensors 10 in which the electrodes, traces and contact pads are comprised of electrically conductive thin films (for instance, noble metals, carbon ink, and silver paste, as non-limiting examples), the resistivity of the conductive traces 14c,16c that connect the contact zone 22 to the reaction zone 20 can amount to several hundred Ohms or more. This parasitic resistance causes a potential drop along the length of the traces 14c,16c, such that the potential presented to the measurement electrodes 14a,16a in the reaction zone 20 is considerably less than the potential applied by the test meter to the contact pads 14b,16b of the test strip 10 in the contact zone 22. Because the impedance of the reaction taking place within the reaction zone 20 can be within an order of magnitude of the parasitic resistance of the traces 14c,16c, the signal being measured can have a significant offset due to the I-R (current x resistance) drop induced by the traces. If this offset varies from test strip to test strip, then noise is added to the measurement result. Furthermore, physical damage to the test strip 10, such as abrasion, cracks, scratches, chemical degradation, etc. can occur during manufacturing, shipping, storage and/or user mishandling. These defects can damage the conductive areas 14,16 to the point that they present an extremely high resistance or even an open circuit. Such increases in the trace resistance can prevent the test meter from performing an accurate test.

SUMMARY

A test strip for measuring a signal of interest in a biological fluid when the test strip is mated to an appropriate test meter, wherein the test strip and the test meter include structures to verify the integrity of the test strip traces, to measure the parasitic resistance of the test strip traces, and to provide compensation in the voltage applied to the test strip to account for parasitic resistive losses in the test strip traces. In addition, conductive traces are positioned to ensure structural interrogation of all electrodes and traces present upon the test strip.

BRIEF DESCRIPTION OF THE DRAWINGS

The invention will be further described, by way of example only, with reference to the accompanying drawings, in which:

FIG. 2 is a schematic plan view of a first embodiment test strip according to the present invention.

FIG. 3 is a schematic diagram of a first embodiment electronic test circuit for use with the first embodiment test strip of FIG. 2.

FIG. 8 is a schematic plan view of a second embodiment test strip according to the present invention.

FIG. 9 is a schematic diagram of a second embodiment electronic test circuit for use with the second embodiment test strip of FIG. 8.

DETAILED DESCRIPTION OF THE SELECTED EMBODIMENTS

Figure 1:
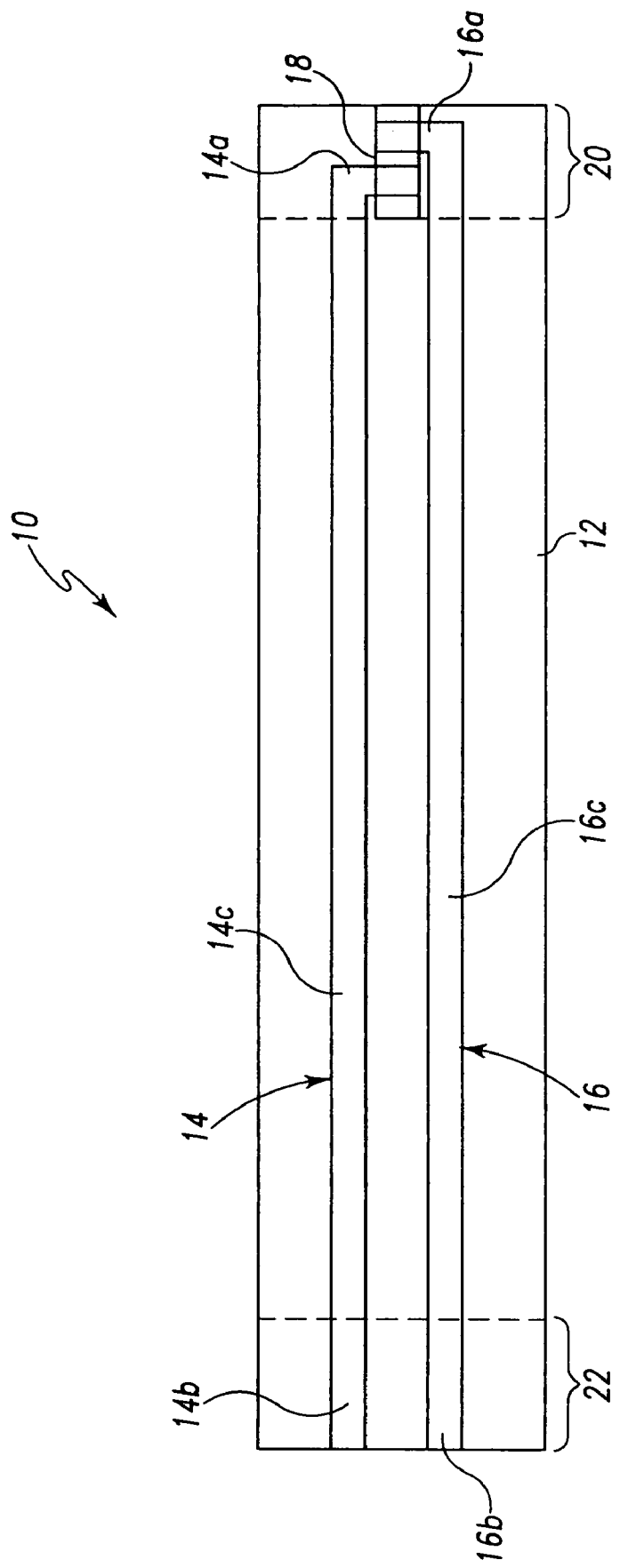
FIG. 1 is schematic plan view of a typical prior art test strip for use in measuring the concentration of an analyte of interest in a biological fluid.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. In particular, although the invention is discussed in terms of a blood glucose meter, it is contemplated that the invention can be used with devices for measuring other analytes and other sample types. Such alternative embodiments require certain adaptations to the embodiments discussed herein that would be obvious to those skilled in the art.

Although the system and method of the present invention may be used with test strips having a wide variety of designs and made with a wide variety of construction techniques and processes, a first embodiment electrochemical test strip of the present invention is illustrated schematically in FIG. 2, and indicated generally at 200. Portions of test strip 200 which are substantially identical to those of test strip 10 are marked with like reference designators. Referring to FIG. 2, the test strip 200 comprises a bottom substrate 12 formed from an opaque piece of 350 µm thick polyester (such as Melinex 329 available from DuPont) coated on its top surface with a 50 nm conductive gold layer (for instance by sputtering or vapor deposition, by way of non-limiting example). Electrodes, connecting traces and contact pads therefor are then patterned in the conductive layer by, for example, a laser ablation process. One embodiment of a laser ablation process is performed by means of an excimer laser which passes through a chrome-on-quartz mask. The mask pattern defined by chrome causes parts of the laser field to be reflected while allowing other parts of the field to pass through the quartz, creating a pattern on the gold which is evaporated where contacted by the laser light. The laser ablation process is described in greater detail hereinbelow. For example, working 214a, counter 216a, and counter sense 224a electrodes may be formed as shown and coupled to respective measurement contact pads 214b, 216b and 224b by means of respective traces 214c, 216c and 224c. These contact pads 214b, 216b and 224b provide a conductive area upon the test strip 200 to be contacted by a connector contact of the test meter (not shown) once the test strip 200 is inserted into the test meter, as is well known in the art.

FIGS. 2 and 3 illustrate an embodiment of the present invention that improves upon the prior art test strip designs by allowing for compensation of parasitic I-R drop in the counter electrode line of the test strip. It will be appreciated that the test strip 200 of FIG. 2 is substantially identical to the prior art test strip 10 of FIG. 1, except for the addition of the counter sense electrode 224a, contact pad 224b, and trace 224c. Provision of the counter sense line 224 allows the test meter (as described hereinbelow) to compensate for parasitic resistance between the contact pads 216b,224b. Note that the embodiment of FIG. 2 when used with the circuit of FIG. 3 only compensates for the I-R drop on the counter electrode side of the test strip 200. Parasitic resistance on the working electrode side of the test strip 200 cannot be detected using this circuitry, although it could be replicated on the working electrode side if desired, as will be apparent to those skilled in the art with reference to the present diclosure. Further methods for compensating for parasitic resistance on both the working and counter sides of the test strip are presented hereinbelow. The counter sense line of FIG. 2 therefore allows the test meter to compensate for any parasitic resistance potential drop in the counter line 216, as explained in greater detail with respect to FIG. 3.

Referring now to FIG. 3, there is shown a schematic electrical circuit diagram of a first embodiment electrode compensation circuit (indicated generally at 300) housed within the test meter. As indicated, the circuit couples to contact pads 214b, 216b and 224b when the test strip 200 is inserted into the test meter. As will be appreciated by those skilled in the art, a voltage potential is applied to the counter electrode contact pad 216b, which will produce a current between the counter electrode 216a and the working electrode 214a that is proportional to the amount of analyte present in the biological sample applied to the reagent 18. The current from working electrode 214a is transmitted to working electrode contact pad. 214b by means of working electrode trace 214c and provided to a current-to-voltage amplifier 310. The analog output voltage of amplifier 310 is converted to a digital signal by analog-to-digital converter (A/D) 312. This digital signal is then processed by microprocessor 314 according to a previously stored program in order to determine the concentration of analyte within the biological sample applied to the test strip 200. This concentration is displayed to the user by means of an appropriate output device 316, such as a liquid crystal display (LCD) screen.

Microprocessor 314 also outputs a digital signal indicative of the voltage potential to be applied to the counter electrode contact pad 216b. This digital signal is converted to an analog voltage signal by digital-to-analog converter (D/A) 318. The analog output of D/A 318 is applied to a first input of an operational amplifier 320. A second input of the operational amplifier 320 is coupled to counter sense electrode contact pad 224b. The output of operational amplifier 320 is coupled to the counter electrode contact pad 216b.

Operational amplifier 320 is connected in a voltage follower configuration, in which the amplifier will adjust its output (within its physical limits of operation) until the voltage appearing at its second input is equal to the commanded voltage appearing at its first input. The second input of operational amplifier 320 is a high impedance input, therefore substantially no current flows in counter sense line 224. Since substantially no current flows, any parasitic resistance in counter sense line 224 will not cause a potential drop, and the voltage appearing at the second input of operational amplifier 320 is substantially the same as the voltage at counter sense electrode 224a, which is in turn substantially the same as the voltage appearing at counter electrode 216a due to their close physical proximity. Operational amplifier 320 therefore acts to vary the voltage potential applied to the counter electrode contact pad 216b until the actual voltage potential appearing at the counter electrode 216a (as fed back over counter sense line 224) is equal to the voltage potential commanded by the microprocessor 314. Operational amplifier 320 therefore automatically compensates for any potential drop caused by the parasitic resistance in the counter electrode trace 216c, and the potential appearing at the counter electrode 216a is the desired potential. The calculation of the analyte concentration in the biological sample from the current produced by the working electrode is therefore made more accurate, since the voltage that produced the current is indeed the same voltage commanded by the microprocessor 314. Without the compensation for parasitic resistance voltage drops provided by the circuit 300, the microprocessor 314 would analyze the resulting current under the mistaken presumption that the commanded voltage was actually applied to the counter electrode 216a.

Many methods are available for preparing test strips having multiple electrodes, such as carbon ink printing, silver paste silk-screening, scribing metalized plastic, electroplating, chemical plating, and photo-chemical etching, by way of non-limiting example. One method of preparing a test strip having additional electrode sense lines as described herein is by the use of laser ablation techniques. Examples of the use of these techniques in preparing electrodes for biosensors are described in U.S. patent application Ser. No. 09/866,030, "Biosensors with Laser Ablation Electrodes with a Continuous Coverlay Channel" filed May 25, 2001, and in U.S. patent application Ser. No. 09/411,940, entitled "Laser Defined Features for Patterned Laminates and Electrode," filed Oct. 4, 1999, both disclosures incorporated herein by reference. Laser ablation is useful in preparing test strips according to the present invention because it allows conductive areas having extremely small feature sizes to be accurately manufactured in a repeatable manner. Laser ablation provides a means for adding the extra sense lines of the present invention to a test strip without increasing the size of the test strip.

It is desirable in the present invention to provide for the accurate placement of the electrical components relative to one another and to the overall biosensor. In one embodiment, the relative placement of components is achieved, at least in part, by the use of broad field laser ablation that is performed through a mask or other device that has a precise pattern for the electrical components. This allows accurate positioning of adjacent edges, which is further enhanced by the close tolerances for the smoothness of the edges.

Figure 4:
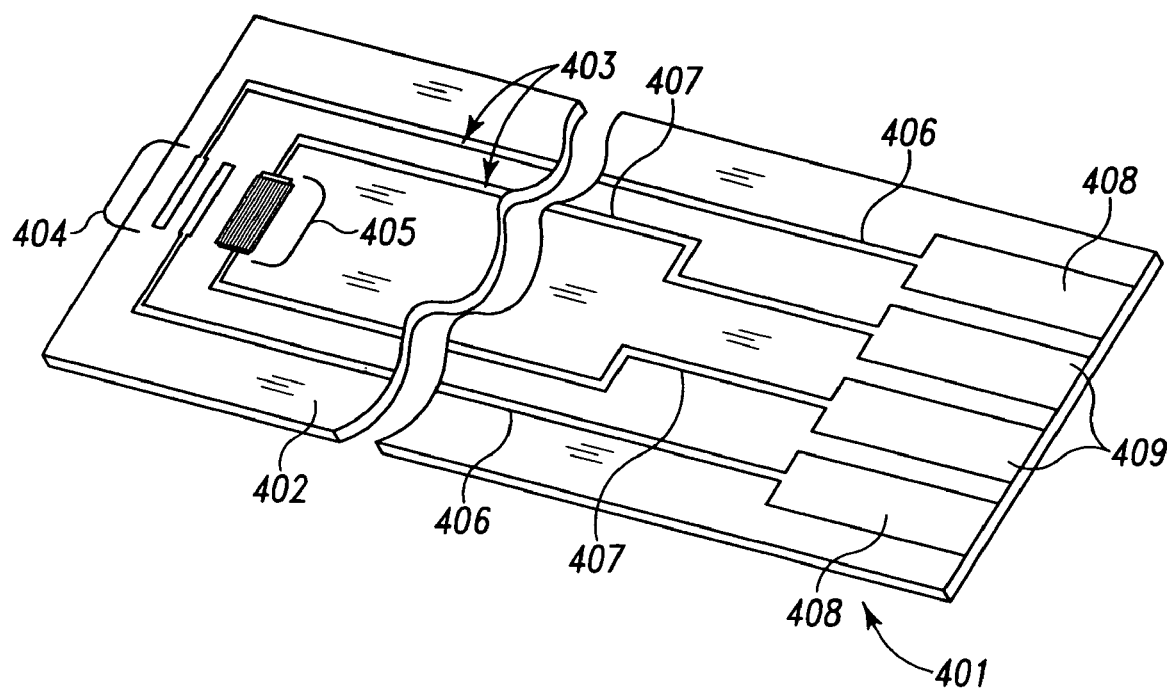
FIG. 4 is an exploded assembly view of a second typical test strip for use in measuring the concentration of an analyte of interest in a biological fluid.

FIG. 4 illustrates a simple biosensor 401 useful for illustrating the laser ablation process of the present invention, including a substrate 402 having formed thereon conductive material 403 defining electrode systems comprising a first electrode set 404 and a second electrode set 405, and corresponding traces 406, 407 and contact pads 408, 409, respectively. Note that the biosensor 401 is used herein for purposes of illustrating the laser ablation process, and that it is not shown as incorporating the sense lines of the present invention. The conductive material 403 may contain pure metals or alloys, or other materials, which are metallic conductors. In some embodiments, the conductive material is absorptive at the wavelength of the laser used to form the electrodes and of a thickness amenable to rapid and precise processing. Non-limiting examples include aluminum, carbon, copper, chromium, gold, indium tin oxide (ITO), palladium, platinum, silver, tin oxide/gold, titanium, mixtures thereof, and alloys or metallic compounds of these elements. In some embodiments, the conductive material includes noble metals or alloys or their oxides. Other embodiments use conductive materials such as gold, palladium, aluminum, titanium, platinum, ITO and chromium. The conductive material ranges in thickness from about 10 nm to 80 nm. Some embodiments use thickness ranges between 30 nm to 70 nm, others use thicknesses at 50 nm. It is appreciated that the thickness of the conductive material depends upon the transmissive property of the material and other factors relating to use of the biosensor.

While not illustrated, it is appreciated that the resulting patterned conductive material can be coated or plated with additional metal layers. For example, the conductive material may be copper, which is then ablated with a laser into an electrode pattern; subsequently, the copper may be plated with a titanium/tungsten layer, and then a gold layer, to form the desired electrodes. In most embodiments, a single layer of conductive material is used, which lies on the base 402. Although not generally necessary, it is possible to enhance adhesion of the conductive material to the base, as is well known in the art, by using seed or ancillary layers such as chromium nickel or titanium. In some embodiments, biosensor 401 has a single layer of gold, palladium, platinum or ITO.

Figure 5:
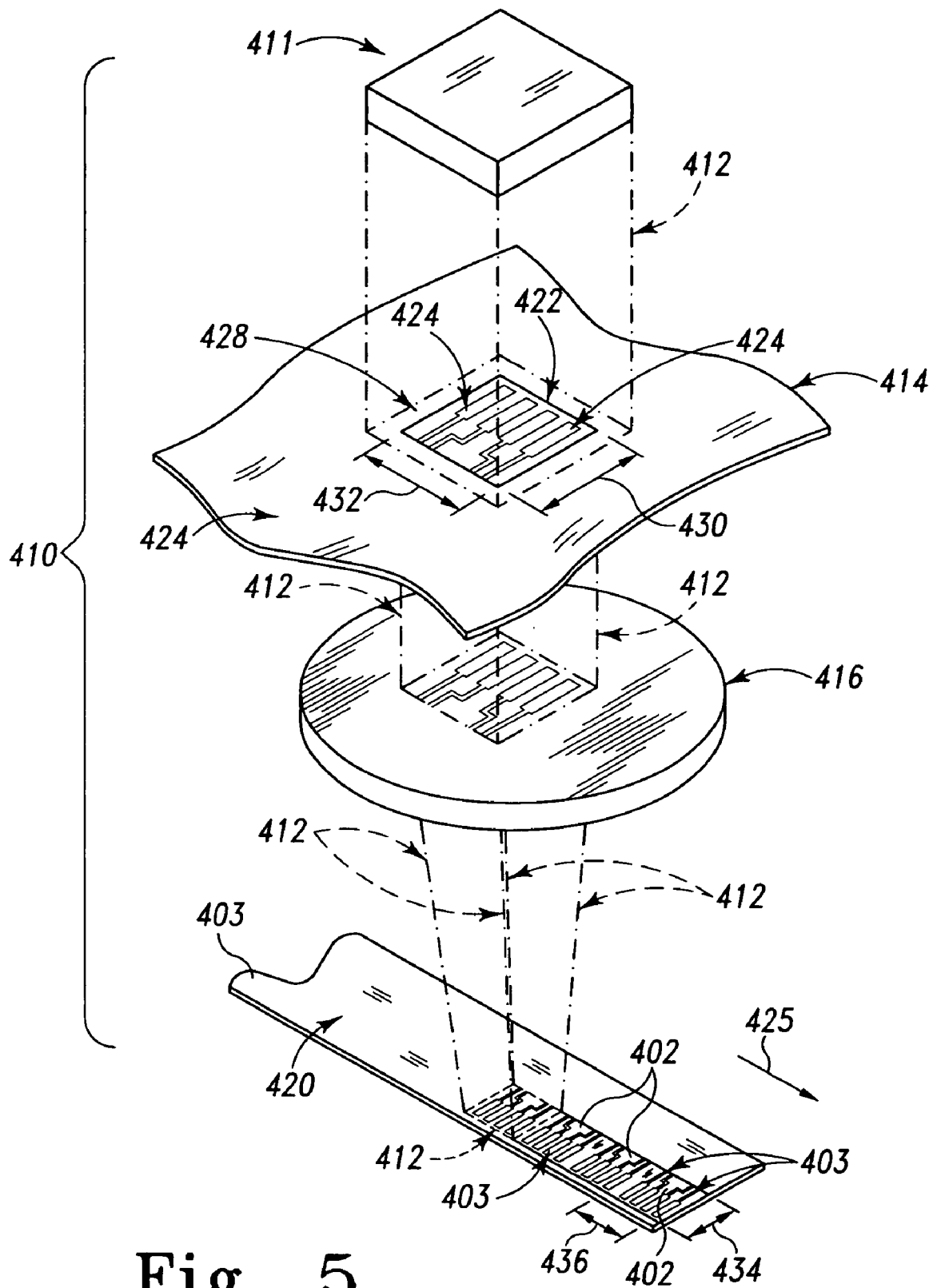
FIG. 5 illustrates a view of an ablation apparatus suitable for use with the present invention.
Figure 6:
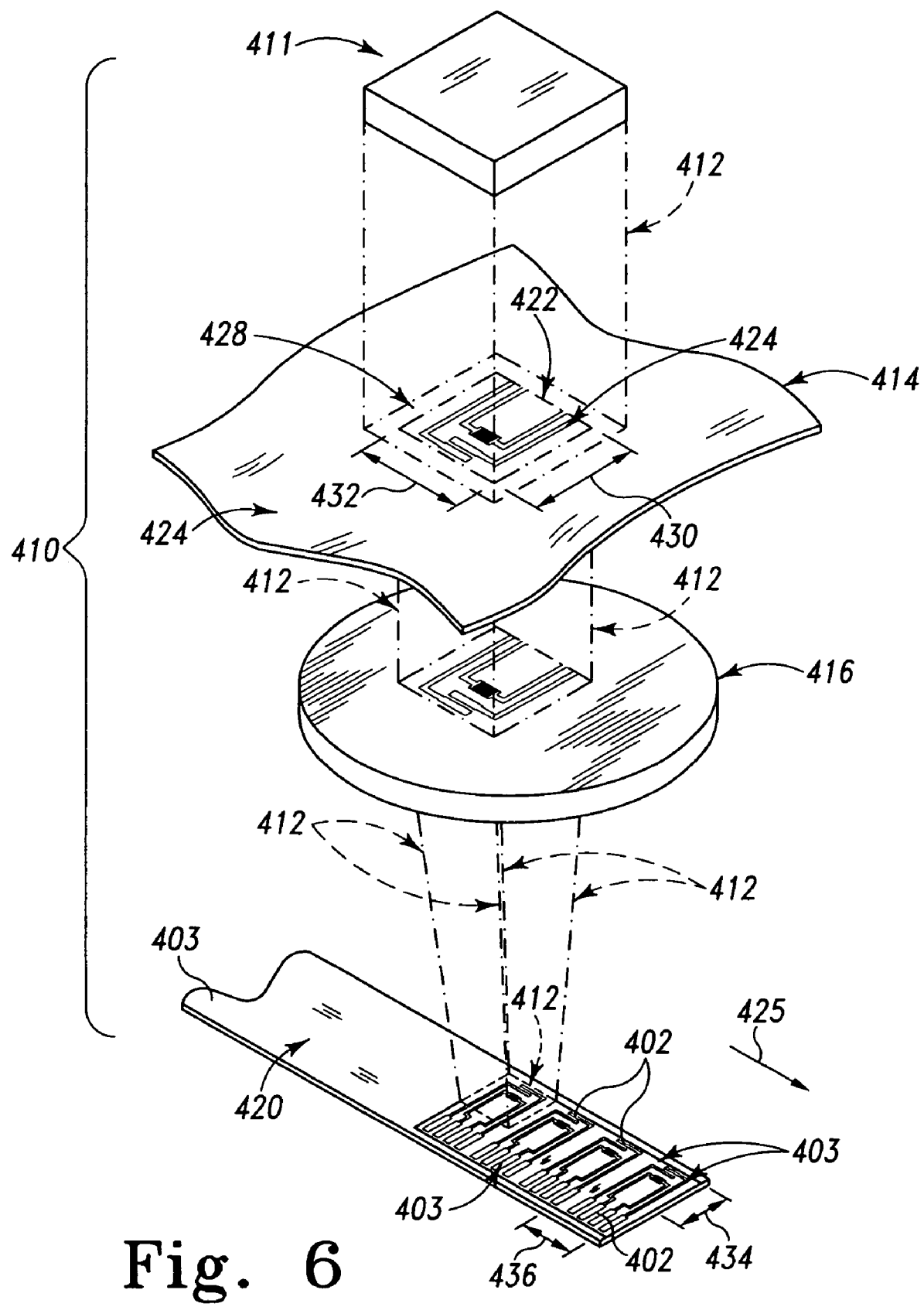
FIG. 6 is a view of the laser ablation apparatus of FIG. 5 showing a second mask.
Figure 7:
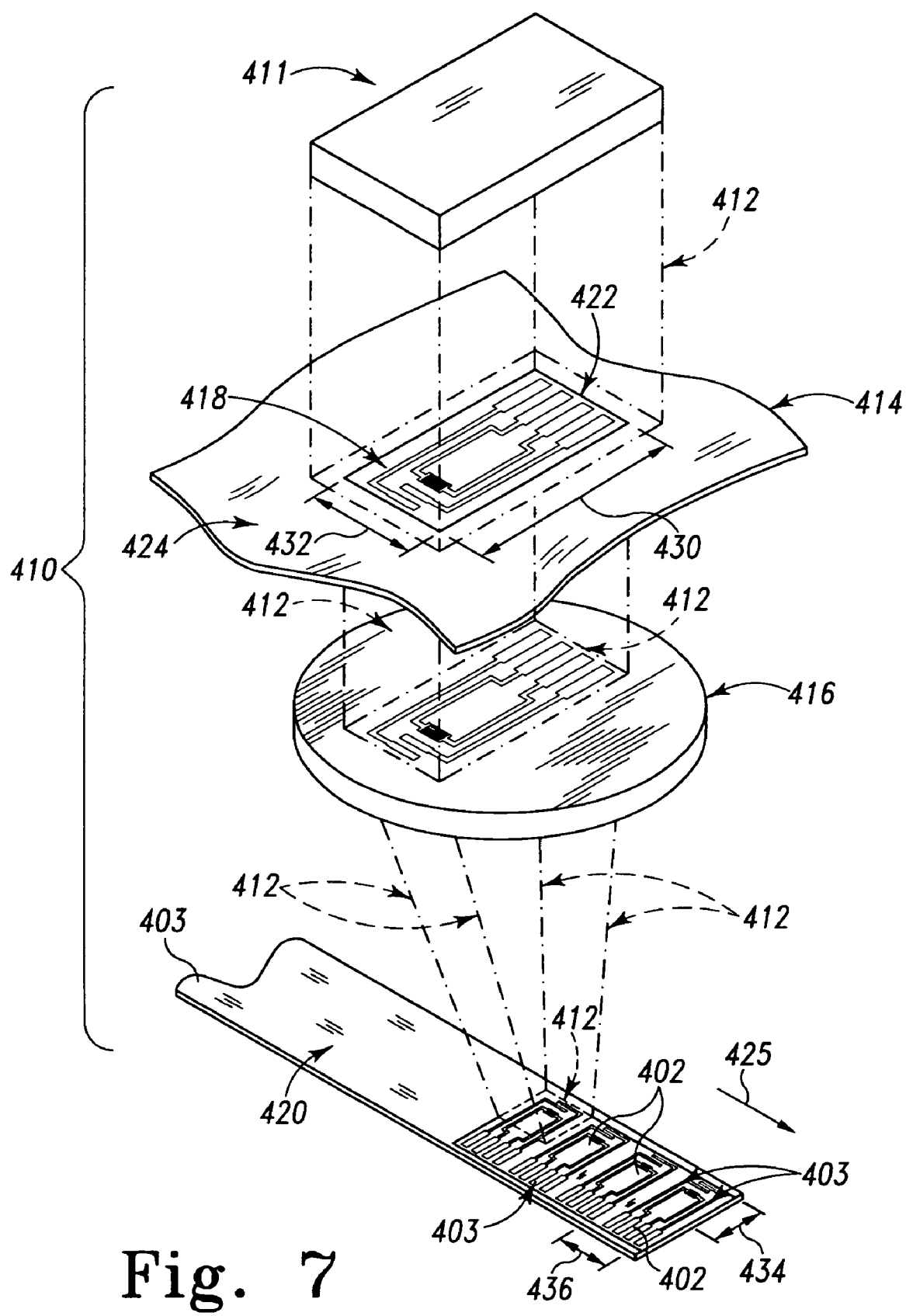
FIG. 7 is a view of an ablation apparatus suitable for use with the present invention.

Biosensor 401 is illustratively manufactured using two apparatuses 10, 10', shown in FIGS. 4, 6 and 7, respectively. It is appreciated that unless otherwise described, the apparatuses 410, 410' operate in a similar manner. Referring first to FIG. 5, biosensor 401 is manufactured by feeding a roll of ribbon 420 having an 80 nm gold laminate, which is about 40 mm in width, into a custom fit broad field laser ablation apparatus 410. The apparatus 410 comprises a laser source 411 producing a beam of laser light 412, a chromium-plated quartz mask 414, and optics 416. It is appreciated that while the illustrated optics 416 is a single lens, optics 416 can be a variety of lenses that cooperate to make the light 412 in a pre-determined shape.

A non-limiting example of a suitable ablation apparatus 410 (FIGS. 5-6) is a customized MicrolineLaser 200-4 laser system commercially available from LPKF Laser Electronic GmbH, of Garbsen, Germany, which incorporates an LPX-400, LPX-300 or LPX-200 laser system commercially available from Lambda Physik AG, Göttingen, Germany and a chromium-plated quartz mask commercially available from Infinite Graphics, Minneapolis, Minn.

For the MicrolineLaser 200-4 laser system (FIGS. 5-6), the laser source 411 is a LPX-200 KrF-UV-laser. It is appreciated, however, that higher wavelength UV lasers can be used in accordance with this disclosure. The laser source 411 works at 248 nm, with a pulse energy of 600 mJ, and a pulse repeat frequency of 50 Hz. The intensity of the laser beam 412 can be infinitely adjusted between 3% and 92% by a dielectric beam attenuator (not shown). The beam profile is 27×15 mm² (0.62 sq. inch) and the pulse duration 25 ns. The layout on the mask 414 is homogeneously projected by an optical elements beam expander, homogenizer, and field lens (not shown). The performance of the homogenizer has been determined by measuring the energy profile. The imaging optics 416 transfer the structures of the mask 414 onto the ribbon 420. The imaging ratio is 2:1 to allow a large area to be removed on the one hand, but to keep the energy density below the ablation point of the applied chromium mask on the other hand. While an imaging of 2:1 is illustrated, it is appreciated that the any number of alternative ratios are possible in accordance with this disclosure depending upon the desired design requirements. The ribbon 420 moves as shown by arrow 425 to allow a number of layout segments to be ablated in succession.

The positioning of the mask 414, movement of the ribbon 420, and laser energy are computer controlled. As shown in FIG. 5, the laser beam 412 is projected onto the ribbon 420 to be ablated. Light 412 passing through the clear areas or windows 418 of the mask 414 ablates the metal from the ribbon 420. Chromium coated areas 424 of the mask 414 blocks the laser light 412 and prevent ablation in those areas, resulting in a metallized structure on the ribbon 420 surface. Referring now to FIG. 6, a complete structure of electrical components may require additional ablation steps through a second mask 414'. It is appreciated that depending upon the optics and the size of the electrical component to be ablated, that only a single ablation step or greater than two ablation steps may be necessary in accordance with this disclosure. Further, it is appreciated that instead of multiple masks, that multiple fields may be formed on the same mask in accordance with this disclosure.

Specifically, a second non-limiting example of a suitable ablation apparatus 410' (FIG. 7) is a customized laser system commercially available from LPKF Laser Electronic GmbH, of Garbsen, Germany, which incorporates a Lambda STEEL (Stable energy eximer laser) laser system commercially available from Lambda Physik AG, Göttingen, Germany and a chromium-plated quartz mask commercially available from Infinite Graphics, Minneapolis, Minn. The laser system features up to 1000 mJ pulse energy at a wavelength of 308 nm. Further, the laser system has a frequency of 100 Hz. The apparatus 410' may be formed to produce biosensors with two passes as shown in FIGS. 5 and 6, but in some embodiments its optics permit the formation of a 10×40 mm pattern in a 25 ns single pass.

While not wishing to be bound to a specific theory, it is believed that the laser pulse or beam 412 that passes through the mask 414, 414', 414" is absorbed within less than 1 μm of the surface 402 on the ribbon 420. The photons of the beam 412 have an energy sufficient to cause photo-dissociation and the rapid breaking of chemical bonds at the metal/polymer interface. It is believed that this rapid chemical bond breaking causes a sudden pressure increase within the absorption region and forces material (metal film 403) to be ejected from the polymer base surface. Since typical pulse durations are around 20-25 nanoseconds, the interaction with the material occurs very rapidly and thermal damage to edges of the conductive material 403 and surrounding structures is minimized. The resulting edges of the electrical components have high edge quality and accurate placement as contemplated by the present invention.

Fluence energies used to remove or ablate metals from the ribbon 420 are dependent upon the material from which the ribbon 420 is formed, adhesion of the metal film to the base material, the thickness of the metal film, and possibly the process used to place the film on the base material, i.e. supporting and vapor deposition. Fluence levels for gold on KALADEX® range from about 50 to about 90 mJ/cm², on polyimide about 100 to about 120 mJ/cm², and on MELINEX® about 60 to about 120 mJ/cm². It is understood that fluence levels less than or greater than the above mentioned can be appropriate for other base materials in accordance with the disclosure.

Patterning of areas of the ribbon 420 is achieved by using the masks 414, 414'. Each mask 414, 414' illustratively includes a mask field 422 containing a precise two-dimensional illustration of a pre-determined portion of the electrode component patterns to be formed. FIG. 5 illustrates the mask field 422 including contact pads and a portion of traces. As shown in FIG. 6, the second mask 414' contains a second corresponding portion of the traces and the electrode patterns containing fingers. As previously described, it is appreciated that depending upon the size of the area to be ablated, the mask 414 can contain a complete illustration of the electrode patterns (FIG. 7), or portions of patterns different from those illustrated in FIGS. 5 and 6 in accordance with this disclosure. It is contemplated that in one aspect of the present invention, the entire pattern of the electrical components on the test strip are laser ablated at one time, i.e., the broad field encompasses the entire size of the test strip (FIG. 7). In the alternative, and as illustrated in FIGS. 5 and 6, portions of the entire biosensor are done successively.

While mask 414 will be discussed hereafter, it is appreciated that unless indicated otherwise, the discussion will apply to masks 414', 414" as well. Referring to FIG. 5, areas 424 of the mask field 422 protected by the chrome will block the projection of the laser beam 412 to the ribbon 420. Clear areas or windows 418 in the mask field 422 allow the laser beam 412 to pass through the mask 414 and to impact predetermined areas of the ribbon 420. As shown in FIG. 5, the clear area 418 of the mask field 422 corresponds to the areas of the ribbon 420 from which the conductive material 403 is to be removed.

Further, the mask field 422 has a length shown by line 430 and a width as shown by line 432. Given the imaging ratio of 2:1 of the LPX-200, it is appreciated that the length 30 of the mask is two times the length of a length 434 of the resulting pattern and the width 432 of the mask is two times the width of a width 436 of the resulting pattern on ribbon 420. The optics 416 reduces the size of laser beam 412 that strikes the ribbon 420. It is appreciated that the relative dimensions of the mask field 422 and the resulting pattern can vary in accordance with this disclosure. Mask 414' (FIG. 6) is used to complete the two-dimensional illustration of the electrical components.

Continuing to refer to FIG. 5, in the laser ablation apparatus 410 the excimer laser source 411 emits beam 412, which passes through the chrome-on-quartz mask 414. The mask field 422 causes parts of the laser beam 412 to be reflected while allowing other parts of the beam to pass through, creating a pattern on the gold film where impacted by the laser beam 412. It is appreciated that ribbon 420 can be stationary relative to apparatus 410 or move continuously on a roll through apparatus 410. Accordingly, non-limiting rates of movement of the ribbon 420 can be from about 0 m/min to about 100 m/min, and in some embodiments about 30 m/min to about 60 m/min. It is appreciated that the rate of movement of the ribbon 420 is limited only by the apparatus 410 selected and may well exceed 100 m/min depending upon the pulse duration of the laser source 411 in accordance with the present disclosure.

Once the pattern of the mask 414 is created on the ribbon 420, the ribbon is rewound and fed through the apparatus 410 again, with mask 414' (FIG. 6). It is appreciated, that alternatively, laser apparatus 410 could be positioned in series in accordance with this disclosure. Thus, by using masks 414, 414', large areas of the ribbon 420 can be patterned using step-and-repeat processes involving multiple mask fields 422 in the same mask area to enable the economical creation of intricate electrode patterns and other electrical components on a substrate of the base, the precise edges of the electrode components, and the removal of greater amounts of the metallic film from the base material.

The second embodiment of the present invention illustrated in FIGS. 8 and 9 improve upon the prior art by providing for I-R drop compensation of both the working and counter electrode leads on the test strip. Referring now to FIG. 8, there is schematically illustrated a second embodiment test strip configuration of the present invention, indicated generally at 800. The test strip 800 comprises a bottom substrate 12 coated on its top surface with a 50 nm conductive gold layer (for instance by sputtering or vapor deposition, by way of non-limiting example). Electrodes, connecting traces and contact pads therefor are then patterned in the conductive layer by a laser ablation process as described hereinabove. For example, working 814a, working sense 826a, counter 216a, and counter sense 224a electrodes may be formed as shown and coupled to respective measurement contact pads 814b, 826b, 216b and 224b by means of respective traces 814c, 826c, 216c and 224c. These contact pads 814b, 826b, 216b and 224b provide a conductive area upon the test strip 800 to be contacted by a connector contact of the test meter (not shown) once the test strip 800 is inserted into the test meter.

It will be appreciated that the test strip 800 of FIG. 8 is substantially identical to the first embodiment test strip 200 of FIG. 2, except for the addition of the working sense electrode 826a, contact pad 826b, and trace 826c. Provision of the working sense line 826 allows the test meter to compensate for any I-R drop caused by the contact resistance of the connections to the contact pads 814b and 216b, and to compensate for the trace resistance of traces 814c and 216c.

Referring now to FIG. 9, there is shown a schematic electrical circuit diagram of a second embodiment electrode compensation circuit (indicated generally at 900) housed within the test meter. As indicated, the circuit couples to contact pads 826b, 814b, 216b and 224b when the test strip 800 is inserted into the test meter. As will be appreciated by those skilled in the art, a voltage potential is applied to the counter electrode contact pad 216b, which will produce a current between the counter electrode 216a and the working electrode 814a that is proportional to the amount of analyte present in the biological sample applied to the reagent 18. The current from working electrode 814a is transmitted by working electrode trace 814c to working electrode contact pad 814b and provided to current-to-voltage amplifier 310. The analog output voltage of amplifier 310 is converted to a digital signal by A/D 312. This digital signal is then processed by microprocessor 314 according to a previously stored program in order to determine the concentration of the analyte of interest within the biological sample applied to the test strip 800. This concentration is displayed to the user by means of LCD output device 316.

Microprocessor 314 also outputs a digital signal indicative of the voltage potential to be applied to the counter electrode contact pad 216b. This digital signal is converted to an analog voltage signal by D/A 318. The analog output of D/A 318 is applied to a first input of an operational amplifier 320. A second input of the operational amplifier 320 is coupled to an output of operational amplifier 910. Operational amplifier 910 is connected in a difference amplifier configuration using an instrumentation amplifier. A first input of operational amplifier 910 is coupled to working sense electrode contact pad 826b, while a second input of operational amplifier 910 is coupled to counter sense electrode contact pad 224b. The output of operational amplifier 320 is coupled to the counter electrode contact pad 216b.

Operational amplifier 320 is connected in a voltage follower configuration, in which the amplifier will adjust its output (within its physical limits of operation) until the voltage appearing at its second input is equal to the commanded voltage appearing at its first input. Both inputs of operational amplifier 910 are high impedance inputs, therefore substantially no current flows in counter sense line 224 or working sense line 826. Since substantially no current flows, any parasitic resistance in counter sense line 224 or working sense line 826 will not cause a potential drop, and the voltage appearing across the inputs of operational amplifier 910 is substantially the same as the voltage across the measurement cell (i.e. across counter electrode 216a and working electrode 814a). Because operational amplifier 910 is connected in a difference amplifier configuration, its output represents the voltage across the measurement cell.

Operational amplifier 320 will therefore act to vary its output (i.e. the voltage potential applied to the counter electrode contact pad 216b) until the actual voltage potential appearing across the measurement cell is equal to the voltage potential commanded by the microprocessor 314. Operational amplifier 320 therefore automatically compensates for any potential drop caused by the parasitic resistance in the counter electrode trace 216c, counter electrode contact 216b, working electrode trace 814c, and working electrode contact 814b, and therefore the potential appearing across the measurement cell is the desired potential. The calculation of the analyte concentration in the biological sample from the current produced by the working electrode is therefore made more accurate.

Figure 10:
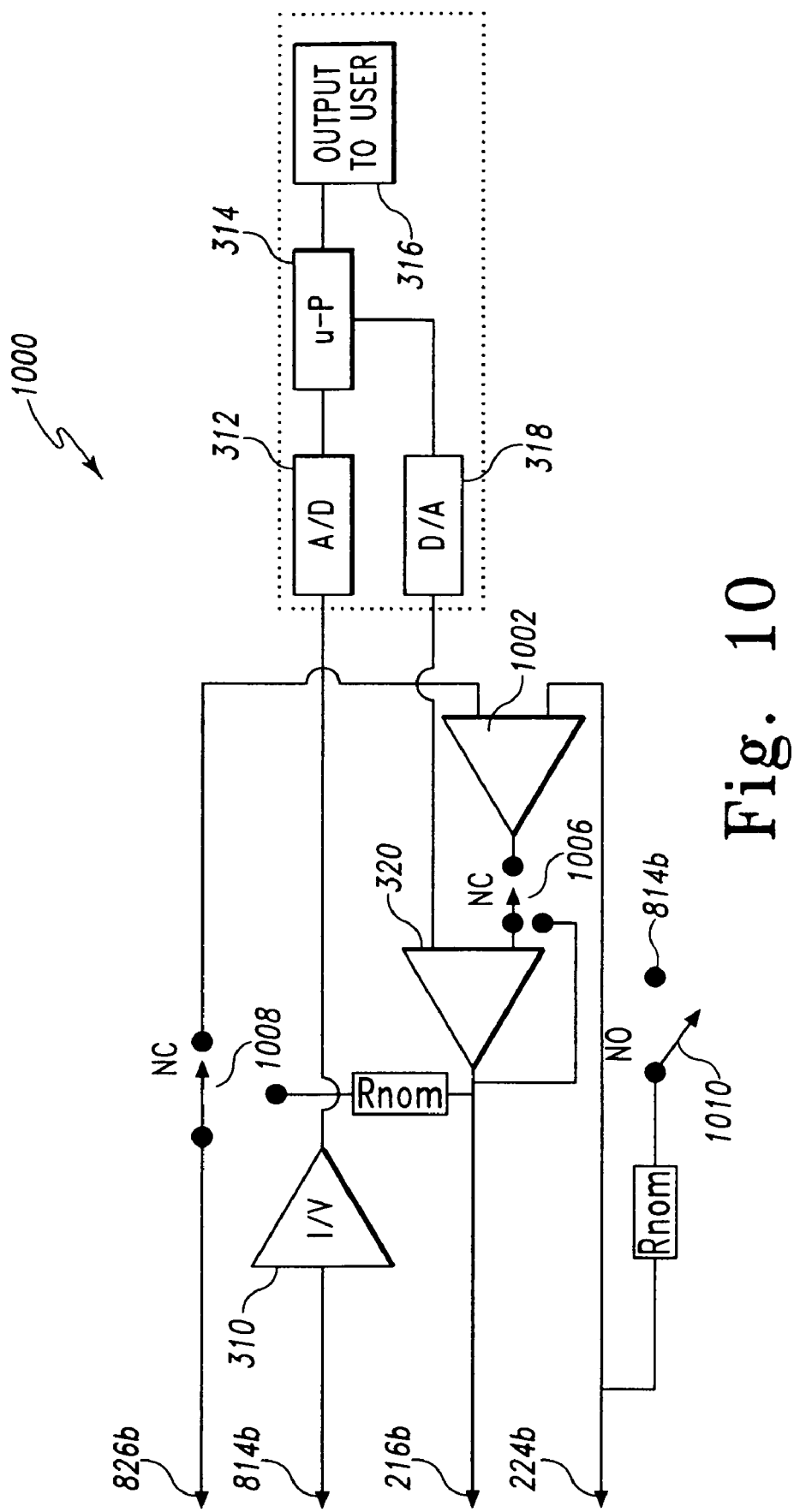
FIG. 10 is a schematic diagram of a third embodiment electronic test circuit for use with the second embodiment test strip of FIG. 8.

FIG. 10, in conjunction with FIG. 8, illustrates a third embodiment of the present invention that improves over the prior art by providing I-R drop compensation for both the working and counter electrode lines, as well as providing verification that the resistance of both the working and counter electrode lines is not above a predetermined threshold in order to assure that the test meter is able to compensate for the I-R drops. Referring now to FIG. 10, there is shown a schematic electrical circuit diagram of a third embodiment electrode compensation circuit (indicated generally at 1000) housed within the test meter. The electrode compensation circuit 1000 works with the test strip 800 of FIG. 8. As indicated, the circuit couples to contact pads 826b, 814b, 216b and 224b when the test strip 800 is inserted into the test meter. As will be appreciated by those skilled in the art, a voltage potential is applied to the counter electrode contact pad 216b, which will produce a current between the counter electrode 216a and the working electrode 814a that is proportional to the amount of analyte present in the biological sample applied to the reagent 18. The current from working electrode 814a is transmitted to working electrode contact pad 814b by working electrode trace 814c and provided to current-to-voltage amplifier 310. The output of current-to-voltage amplifier 310 is applied to the input of instrumentation amplifier 1002 which is configured as a buffer having unity gain when switch 1004 in the closed position. The analog output voltage of amplifier 1002 is converted to a digital signal by A/D 312. This digital signal is then processed by microprocessor 314 according to a previously stored program in order to determine the concentration of analyte within the biological sample applied to the test strip 800. This concentration is displayed to the user by means of LCD output device 316.

Microprocessor 314 also outputs a digital signal indicative of the voltage potential to be applied to the counter electrode contact pad 216b. This digital signal is converted to an analog voltage signal by D/A 318. The analog output of D/A 318 is applied to the input of an operational amplifier 320 that is configured as a voltage follower when switch 1006 is in the position shown. The output of operational amplifier 320 is coupled to the counter electrode contact pad 216b, which will allow measurement of a biological fluid sample applied to the reagent 18. Furthermore, with switches 1006, 1008 and 1010 positioned as illustrated in FIG. 10, the circuit is configured as shown in FIG. 9 and may be used to automatically compensate for parasitic and contact resistance as described hereinabove with respect to FIG. 9.

In order to measure the amount of parasitic resistance in the counter electrode line 216, switch 1008 is placed in the position shown in FIG. 10, switch 1006 is placed in the position opposite that shown in FIG. 10, while switch 1010 is closed. The operational amplifier 320 therefore acts as a buffer with unity gain and applies a voltage potential to counter electrode contact pad 216b through a known resistance $R_{nom}$. This resistance causes a current to flow in the counter electrode line 216 and the counter sense line 224 that is sensed by current-to-voltage amplifier 310, which is now coupled to the current sense line through switch 1010. The output of current-to-voltage amplifier 310 is provided to the microprocessor 314 through A/D 312. Because the value of $R_{nom}$ is known, the microprocessor 314 can calculate the value of any parasitic resistance in the counter sense line 224 and the counter electrode line 216. This parasitic resistance value can be compared to a predetermined threshold stored in the test meter to determine if physical damage has occurred to the test strip 800 or if nonconductive buildup is present on the contact pads to such an extent that the test strip 800 cannot be reliably used to perform a test. In such situations, the test meter may be programmed to inform the user that an alternate test strip should be inserted into the test meter before proceeding with the test.

In order to measure the amount of parasitic resistance in the working electrode line 814, switches 1006 and 1008 are placed in the position opposite that shown in FIG. 10, while switch 1010 is opened. The operational amplifier 320 therefore acts as a buffer with unity gain and applies a voltage potential to working sense contact pad 826b through a known resistance $R_{nom}$. This resistance causes a current to flow in the working sense line 826 and the working electrode line 814 that is sensed by current-to-voltage amplifier 310. The output of current-to-voltage amplifier 310 is provided to the microprocessor 314 through A/D 312. Because the value of $R_{nom}$ is known, the microprocessor 314 can calculate the value of any parasitic resistance in the working sense line 826 and the working electrode line 814. This parasitic resistance value can be compared to a predetermined threshold stored in the test meter to determine if physical damage has occurred to the test strip 800 or if nonconductive buildup is present on the contact pads to such an extent that the test strip 800 cannot be reliably used to perform a test. In such situations, the test meter may be programmed to inform the user that an alternate test strip should be inserted into the test meter before proceeding with the test.

Figure 11:
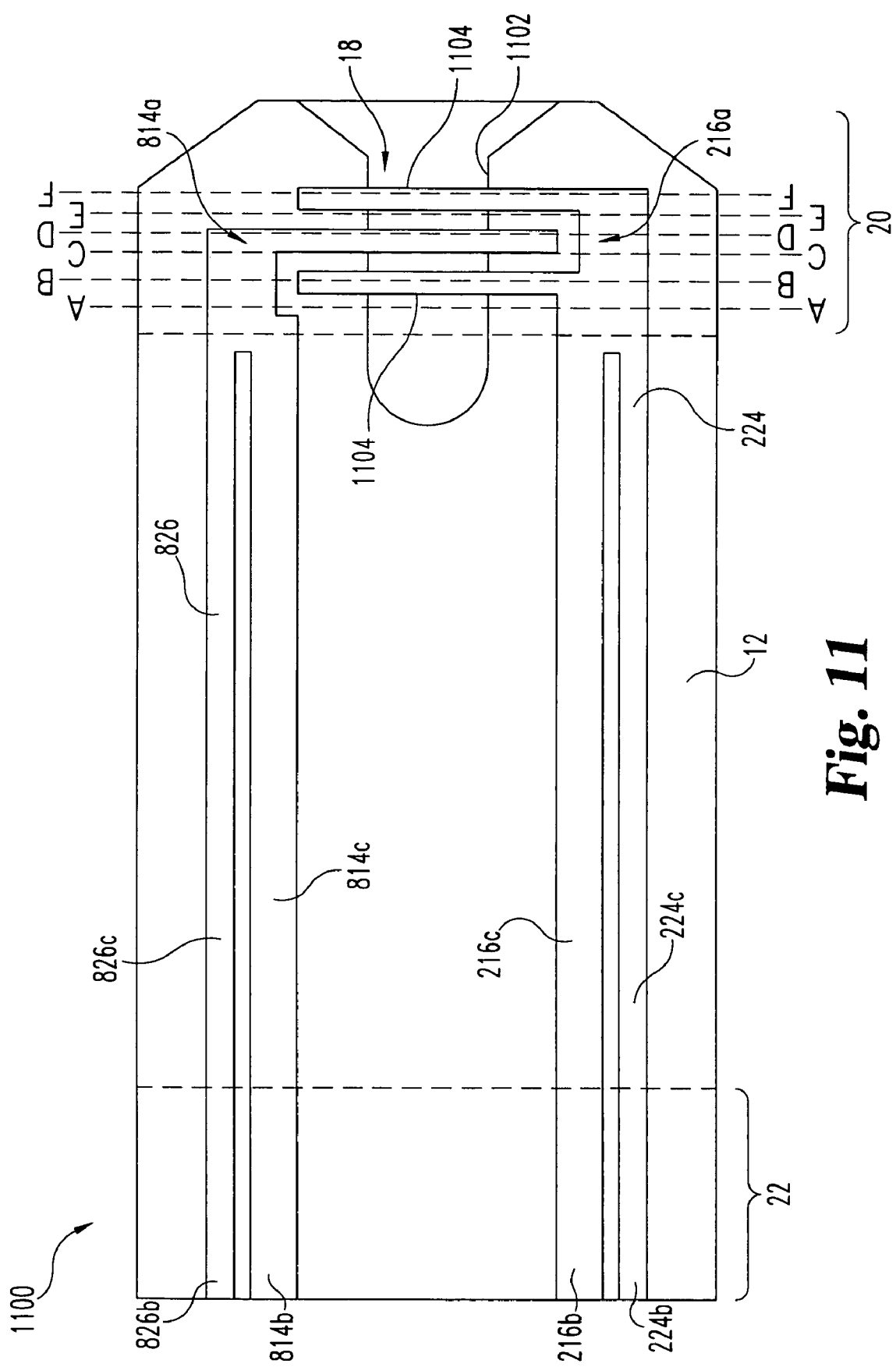
FIG. 11 is a schematic plan view of a third embodiment of a test strip.

FIG. 11 schematically illustrates a third embodiment test strip according to the present invention having I-R drop compensation for both the working electrode and the counter electrode as in FIG. 8. The third embodiment test strip 1100 comprises a bottom substrate 12 coated on its top surface with a 50 nm conductive layer (for instance by sputtering or vapor deposition, by way of non-limiting example). Electrodes, connecting traces and contact pads therefor are then patterned in the conductive layer by a laser ablation process as described hereinabove. As will readily be apparent to those skilled in the art, the test strip of FIG. 11 is similar to the test strip of FIG. 8. Unlike the test strip of FIG. 8, the counter sense line 224 and the working sense line 826 do not extend into the reaction zone 20. In addition, the counter electrode 216a includes a plurality of fingers 1104 instead of just one. In other embodiments, the working electrode 814a also can include a plurality of fingers 1104. Moreover, a capillary space 1102 is provided for drawing the sample into the reaction zone 20 so that it covers portions of the electrodes 216a and 814a.

The design illustrated in FIG. 11 inherently includes some performance limitations. Lines A-A, B-B, C-C, etc. are areas that cannot be interrogated to determine if there are faults in the structural integrity of the electrodes 216a, 814a or the fingers 1104. For example, any physical defect in these areas, such as a scratch that increases the trace resistance or completely severs the trace cannot be detected by the quality assurance checks described hereinabove. This is due to the fact that the sense lines 224c, 826c join respective electrode traces 216c, 814c at points between the test meter and line A-A. Any damage to the test strip 1100 between lines A-A and F-F is therefore outside of the quality assurance test loop and will have no impact upon the I-R drop compensation or parasitic resistance threshold test described hereinabove. The position of the sense lines 826, 224 therefore prevent complete testing of the functionality of the test strip 1100 before a fluid sample is obtained and analyzed. Therefore, the final measurement of the desired characteristic of the fluid sample may be erroneous.

Figure 12:
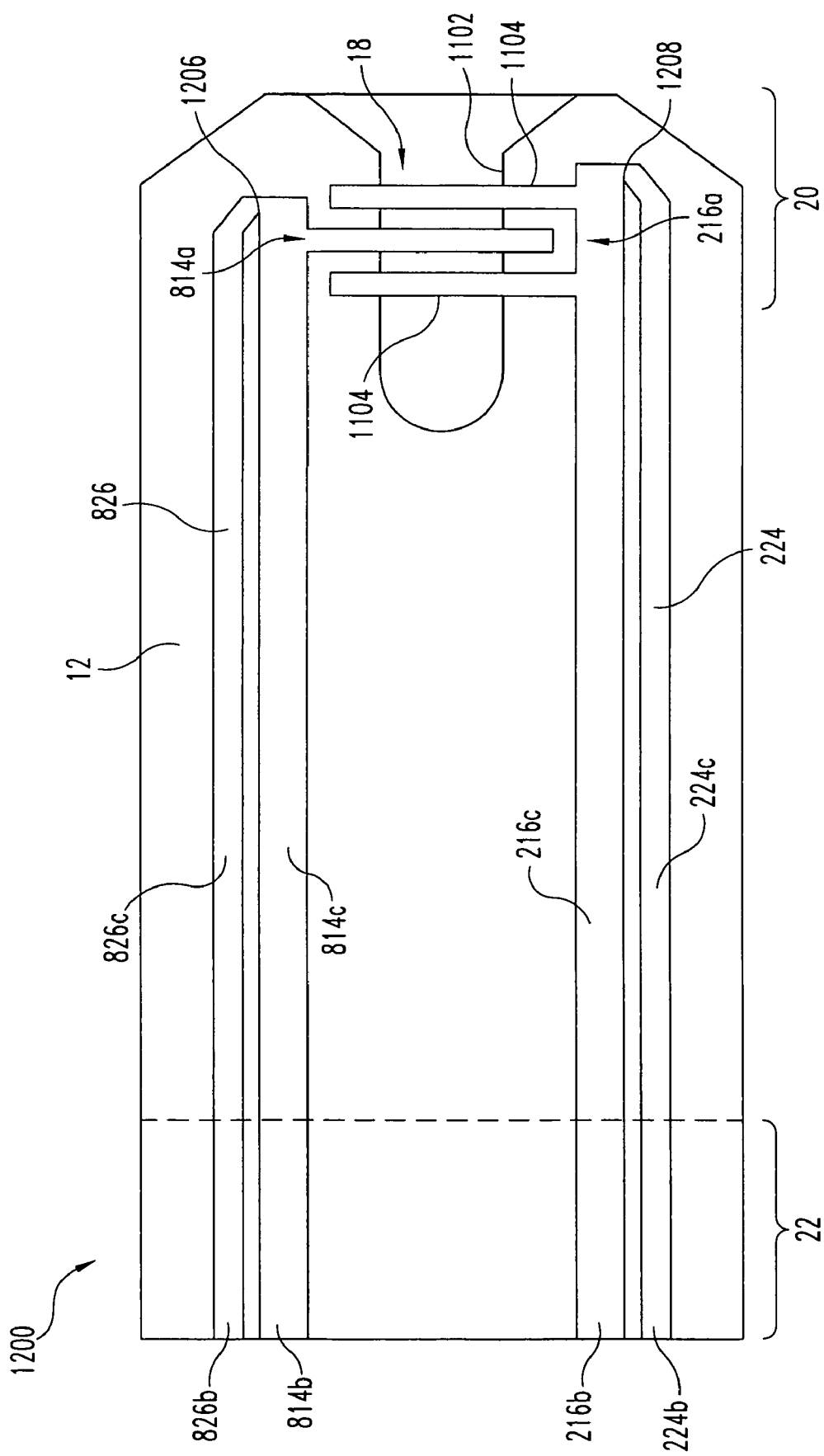
FIG. 12 is a schematic plan view of a fourth embodiment of a test strip.

FIG. 12 illustrates a more robust test strip design to overcome the shortcomings of the design illustrated in FIG. 11. The test strip 1200 includes a working sense line 826 and a counter sense line 224 that have respective points 1206, 1208 where they intersect respective electrodes 814a, 216a. Working sense line 826 and counter sense line 224 are conductive traces formed on substrate 12. The distance (measured in a plane parallel to the longitudinal axis of the test strip) between point 1206 and the power source in the test meter for the test strip 1200 is greater than or equal to the distance between any point on the portion of the working electrode 814a within the reagent 18 and the power source. Similarly, the distance between point 1208 and the power source for the test strip 1200 is greater than or equal to the distance between any point on the portion of the counter electrode 216a within the reagent 18 and the power source. Having working sense line 826 and counter sense line 224 include points 1206, 1208 at these locations enables every point on the test strip 1200 between the power source and the measurement electrode fingers to be interrogated concerning its structural integrity and parasitic resistance. Unlike the design in FIG. 11, the design in FIG. 12 positions the sense lines 224, 826 to enable interrogation of the electrodes 216a, 814a and associated fingers for structural defects. If a defect is found, it can be compensated for or it can be indicated and the test strip 1200 can be disposed of and a new one used. This helps to eliminate errors in the measurement of the desired characteristic of the fluid sample.

All publications, prior applications, and other documents cited herein are hereby incorporated by reference in their entirety as if each had been individually incorporated by reference and fully set forth.

While the invention has been illustrated and described in detail in the drawings and foregoing description, the description is to be considered as illustrative and not restrictive in character. Only certain embodiments deemed helpful in understanding have been shown. All changes and modifications that come within the spirit of the invention are desired to be protected.

What is claimed:

1. An electrochemical test strip powered by a power source comprising:
   a contact zone adapted to be contacted by the power source;
   a first measurement electrode;
   a first conductive trace operatively coupled to the first measurement electrode and to the contact zone, wherein the distance between at least one point on the first conductive trace and the contact zone is greater than or equal to the distance between any point on said first measurement electrode and the contact zone;
   a second conductive trace operatively coupled to the first measurement electrode and to the contact zone;
   a second measurement electrode;
   a third conductive trace operatively coupled to the second measurement electrode; wherein the distance between at least one point on the third conductive trace and the contact zone is greater than or equal to the distance between any point on said second measurement electrode and the contact zone; and
   a fourth conductive trace operatively coupled to the second measurement electrode and to the contact zone.

2. The test strip of claim 1 wherein said first measurement electrode comprises a plurality of fingers.

3. The test strip of claim 2 wherein said fingers include a reagent to create an electrical potential in a fluid sample that is indicative of a desired fluid quality to be measured by the test strip.

4. The test strip of claim 1 wherein said second measurement electrode comprises a plurality of fingers.

5. The test strip of claim 4 wherein said fingers include a reagent to create an electrical potential in a fluid sample that is indicative of a desired fluid quality to be measured by the test strip.

6. An electrochemical test strip powered by a power source comprising:
   a contact zone adapted to be contacted by the power source;
   a measurement electrode;
   a first conductive trace operatively coupled to the measurement electrode and to the contact zone, wherein the distance between at least one point on the first conductive trace and the contact zone is greater than or equal to the distance between any point on said measurement electrode and the contact zone; and
   a second conductive trace operatively coupled to the first measurement electrode and to the contact zone.

7. The test strip of claim 6 wherein said measurement electrode comprises a plurality of fingers.

8. The test strip of claim 7 wherein said fingers further comprise a reagent to create an electrical potential in a fluid sample that is indicative of a desired fluid quality to be measured by the test strip.

9. The test strip of claim 6 further comprising an additional measurement electrode.

10. The test strip of claim 9 further comprising an additional conductive trace operatively coupled to said additional measurement electrode.

11. An electro chemical test strip powered by a power source comprising:
    a reagent disposed within a region on the test strip;
    a contact zone adapted to be contacted by the power source;
    a first measurement electrode;
    a first conductive trace operatively coupled to the first measurement electrode, wherein the distance between at least one point on the first conductive trace and the contact zone is greater than or equal to the distance between any point on said first measurement electrode within said region and the contact zone;
    a second conductive trace operatively coupled to the first measurement electrode and to the contact zone;
    a second measurement electrode;
    a third conductive trace operatively coupled to the second measurement electrode, wherein the distance between at least one point on the third conductive trace and the contact zone is greater than or equal to the distance between any point on said second measurement electrode within said region and the contact zone; and
    a fourth conductive trace operatively coupled to the second measurement electrode and to the contact zone.

12. The test strip of claim 11 wherein said first measurement electrode comprises a plurality of fingers.

13. The test strip of claim 11 wherein said second measurement electrode comprises a plurality of fingers.

14. An electrochemical test strip powered by a power source comprising:
    a reagent disposed within a region on the test strip;
    a contact zone adapted to be contacted by the power source;
    a measurement electrode;
    a first conductive trace operatively coupled to the measurement electrode and to the contact zone, wherein the distance between at least one point on the first conductive trace and the contact zone is greater than or equal to the distance between any point on said measurement electrode within said region and the contact zone; and
    a second conductive trace operatively coupled to the measurement electrode and to the contact zone.

15. The test strip of claim 14 wherein said measurement electrode comprises a plurality of fingers.

16. The test strip of claim 14 further comprising an additional measurement electrode.

17. The test strip of claim 16 further comprising an additional conductive trace operatively coupled to said additional measurement electrode.

18. An electrochemical test strip powered by a power source comprising:
    a contact zone adapted to be contacted by the power source;
    a working electrode;
    a working electrode trace operatively coupled to said working electrode and to the contact zone; and a working sense line operatively coupled to the working electrode and to the contact zone, said working sense line intersecting said working electrode at a first point;

wherein the distance between said first point and said contact zone is greater than or equal to the distance between any point on the working electrode and the contact zone.

19. The test strip of claim 18, further comprising:

a counter electrode;

a counter electrode trace operatively coupled to said counter electrode and to the contact zone; and a counter sense line operatively coupled to the counter electrode and to the contact zone, said counter sense line intersecting said counter electrode at a second point;

wherein the distance between said second point and said contact zone is greater than or equal to the distance between any point on the counter electrode and the contact zone.

* * * * *